US009433452B2

(12) United States Patent
Weiner et al.

(10) Patent No.: US 9,433,452 B2
(45) Date of Patent: Sep. 6, 2016

(54) BONE FIXATION DEVICE AND METHOD

(75) Inventors: Lon Weiner, Rumson, NJ (US); Stuart D. Katchis, Scarsdale, NY (US); John R. Pepper, Cheshire, CT (US)

(73) Assignee: NEXTREMITY SOLUTIONS, LLC, Warsaw, IN (US)

( * ) Notice: Subject to any disclaimer, the term of this patent is extended or adjusted under 35 U.S.C. 154(b) by 790 days.

(21) Appl. No.: 13/566,517

(22) Filed: Aug. 3, 2012

(65) Prior Publication Data
US 2014/0039561 A1 Feb. 6, 2014

(51) Int. Cl.
*A61B 17/66* (2006.01)
*A61B 17/80* (2006.01)

(52) U.S. Cl.
CPC .......... *A61B 17/8004* (2013.01); *A61B 17/80* (2013.01); *A61B 17/809* (2013.01); *A61B 17/8014* (2013.01); *A61B 17/8061* (2013.01)

(58) Field of Classification Search
CPC .............. A61B 17/80; A61B 17/8004; A61B 17/8009; A61B 17/8014; A61B 17/8019; A61B 17/8023; A61B 17/8028; A61B 17/8033; A61B 17/8038; A61B 17/8042; A61B 17/8047; A61B 17/8052; A61B 17/8057; A61B 17/8061; A61B 17/8066; A61B 17/8071; A61B 17/8076; A61B 17/808; A61B 17/8085; A61B 17/809; A61B 17/8095
USPC .............. 606/280–299, 902–906; 623/21.11, 623/21.15
See application file for complete search history.

(56) References Cited

U.S. PATENT DOCUMENTS

| | | | |
|---|---|---|---|
| 5,586,985 A | 12/1996 | Putnam et al. | |
| 5,662,655 A * | 9/1997 | Laboureau et al. | 606/75 |
| 5,674,222 A | 10/1997 | Berger et al. | |
| 5,810,822 A * | 9/1998 | Mortier | 606/86 B |
| 6,648,885 B1 * | 11/2003 | Friesem | A61B 17/7002 606/250 |
| 7,857,836 B2 | 12/2010 | Huebner | |
| 8,177,822 B2 | 5/2012 | Medoff | |
| 2003/0105461 A1 | 6/2003 | Putnam et al. | |
| 2004/0102776 A1 * | 5/2004 | Huebner | A61B 17/1728 606/281 |
| 2004/0210234 A1 | 10/2004 | Coillard-Lavirotte et al. | |
| 2007/0233113 A1 * | 10/2007 | Kaelblein | A61B 17/8061 606/71 |
| 2009/0012569 A1 | 1/2009 | Dall et al. | |
| 2009/0177203 A1 * | 7/2009 | Reiley | A61B 17/8095 606/87 |
| 2009/0254126 A1 * | 10/2009 | Orbay | A61B 17/151 606/282 |
| 2009/0281577 A1 | 11/2009 | Graham et al. | |
| 2009/0318977 A1 | 12/2009 | Di Giacomo | |
| 2011/0208247 A1 | 8/2011 | Modi | |

OTHER PUBLICATIONS

International Search Report and Written Opinion for PCT application No. PCT/US2013/052704, mailed on Oct. 15, 2013.

\* cited by examiner

Primary Examiner — Matthew Lawson
(74) Attorney, Agent, or Firm — John W. Boger

(57) ABSTRACT

In a method and system for corrective surgery of a bone, a bone is cut into a first bone segment and a second bone segment. A plate is positioned over the first bone segment and the second bone segment such that at least one member of the plate is positioned to engage the second bone segment. The at least one member of the plate is inserted into the second bone segment. At least one bone screw is screwed into the first bone segment through at least one compression slot of the plate causing an application of compressive force to secure the first bone segment and the second bone segment to form a corrective construct. The at least one member is positioned at an angle or an offset from the second plate segment.

33 Claims, 25 Drawing Sheets

BONE FIXATION DEVICE AND METHOD

TECHNICAL FIELD

The present disclosure relates to corrective surgery and bone fixation.

BACKGROUND OF THE INVENTION

Bunions are deformities of bones and the joint found on a person's foot, causing pain for any individual having them. A bunion is often associated with hallux abducto valgus, the movement of the great toe laterally. Bunions are progressive and may become painful and debilitating. They are typically caused by poor biomechanics of the foot and footwear which may aggravate the condition.

A bunionectomy is a surgical procedure to remove painful bunions, by reforming the metatarsal. Typically, bunionectomy surgery involves correction of the foot by reconstructing bones and joints. There are numerous ways to correct bunions, the most common of which is the chevron osteotomy. In a chevron osteotomy, the bone is cut at the distal end. The cut is made in a V-shape near the distal metacarpal joint, which allows the entire toe to be moved laterally to the correct alignment. A small metal screw is fixed to the joint to provide stability. The chevron ostetomy is inherently more stable than a single cut osteotomy as two surfaces are in contact, and thus eliminating the likelihood that the bones may slip post operatively.

More specifically, a chevron osteotomy is used for correction of mild to moderate hallux vallgus deformities, allowing for a small reduction of the angle between the first and second metatarsal bones. Thus, the procedure is ideal for bunions that are not particularly pronounced. A V-shaped cut into the distal aspect of the first metatarsal near a metatarsal head allows the distal aspect to be translated (for example, 45 mm) in a lateral direction.

Recurrence of the bunion may occur if the metatarsal experiences a change in alignment after surgery. Thus, secure fixation of any cut metatarsal bone sections is important to ensure a successful bunionectomy fusion procedure. Wolff's law states that bones respond to loading conditions. (Angle Orthod. 2004 February; 74(1):3-15. A 2003 Update of Bone Physiology and Wolff's Law for Clinicians. Frost H M. Source Department of Orthopaedics, Southern Colorado Clinic, 3676 Parker Blvd., Pueblo, Colo. 81008-9000, USA.). An ideal fusion is one having solid and sustained bone contact at the conclusion of a surgical procedure and also keeping sustained bone contact for the weeks following the surgical procedure for the bone remodeling process to unite the bones. Failure to maintain proper fixation to keep sustained bone contact can result in misalignment, malunion, nonunion, and ongoing pain for the patient. Plating requires screws placed in small distal bone segments, which is impractical, as this may split the bone. Staples are low profile, but have limited compression ability, and usually cannot compress more than a millimeter. Additionally, compression is typically only at the tip and not uniform, which may potentially alter the fusion surface contact.

SUMMARY OF THE INVENTION

A method and system for bone fixation is disclosed. More specifically, a method and system for corrective surgery is disclosed.

In an embodiment, a method for corrective surgery of a bone is disclosed. A bone is cut into a first bone segment and a second bone segment. A plate is positioned over the first bone segment and the second bone segment such that at least one member of the plate is positioned to engage the second bone segment. The at least one member of the plate is inserted into the second bone segment. At least one bone screw is screwed into the first bone segment through at least one compression slot of the plate causing an application of compressive force to secure the first bone segment and the second bone segment to form a corrective construct. The at least one member is positioned at an angle or an offset from the second plate segment In an embodiment, a bone fixation system is disclosed. The bone fixation system comprises a plate. The plate comprises a first plate segment and a second plate segment. The first plate segment comprises at least one member for engagement with a second bone segment of the bone. The second plate segment comprises at least one compression slot for receiving at least one male fixation member causing an application of compressive force to secure a first bone segment with the second bone segment to form a corrective construct. The at least one member is positioned at an angle or an offset from the second plate segment In another embodiment, the bone is a first metatarsal bone.

In another embodiment, the bone is cut into the first bone segment and the second bone segment based on a guide placed over the bone.

In another embodiment, the plate is placed over the first bone segment and the second bone segment based on a corrective angle of the first bone segment and the second bone segment.

In another embodiment, a compressive force device applies a compressive force to the at least one member causing engagement of the at least one member with the second bone segment.

In another embodiment, the male fixation member is at least one of a screw, pin, bolt, or nail.

In another embodiment, the male fixation member interacts with the compression slot to cause engagement of the at least one member with the second bone segment.

In another embodiment, a stapling mechanism applies a compressive force to the at least one member causing engagement of the at least one member with the second bone segment.

In another embodiment, an angulation of the at least one member causes the at least one member to move downward as the plate is tightened such that the at least one member does not expulse from the bone.

In another embodiment, the at least one bone screw is screwed into the first bone segment through the at least one hole of the second plate segment to affect compression between the first bone segment and the second bone segment causing the second bone segment to move towards the first bone segment.

In another embodiment, the at least one member comprises fixation means for affixing to the second bone segment.

In another embodiment, the fixation means comprises at least one of: teeth, barbs, or a surface irregularity for securing to the second bone segment.

In another embodiment, the plate is an asymmetric plate.

In another embodiment, the at least one member is configured to be centralized after engagement with the second bone segment, and the at least one member are aligned with respect to each other in a coronal plane at a corrective shift based on the plate.

In another embodiment, the first plate segment and the second plate segment are connected by a hinged connection.

In another embodiment, the first plate segment and the second plate segment have a same thickness.

In another embodiment, the first plate segment and the second plate segment comprise a first material.

In another embodiment, the plate further comprises a third plate segment coupling the first plate segment and the second plate segment. The third plate segment may comprise a first thickness and the first plate segment and the second plate segment may comprise a second thickness. The third plate segment may comprise a first material and the first plate segment and the second plate segment may comprise a second material.

In another embodiment, the at least one member is a tine or a staple.

In another embodiment, the first plate segment and the second plate segment have different thicknesses.

In another embodiment, the at least one member is nearly perpendicular to an axis of the bone.

In an embodiment, a device for fusing joints is disclosed. The device comprises a plate, at least one member, and at least one screw. The plate is for positioning over a first joint and a second joint such that at least one member of the plate is positioned to engage the second joint. The at least one member is for inserting into the second joint. The at least one screw is for screwing into the first joint through at least one compression slot of the plate causing an application of compressive force to secure the first joint and the second joint to form a corrective construct.

In another embodiment, the plate is for positioning over the first joint and the second joint based on a corrective positioning of the first joint and the second joint.

In another embodiment, the first joint and the second joint are positioned at a corrective positioning by translating the second joint laterally.

In another embodiment the at least one member is for inserting into the second joint using compressive force.

In another embodiment, the at least one member is for inserting into the second joint using a stapling mechanism to apply compressive force to the at least one member.

In another embodiment, the at least one screw is for screwing into the first joint through the at least one compression slot to affect compression between the first joint and the second joint causing the second joint to move towards the first joint.

In another embodiment, the at least one member comprises fixation means for affixing to the second joint.

In another embodiment, the at least one member is at least one of a tine or a staple.

In an embodiment, a bone fixation system is disclosed. The bone fixation system comprises a plate comprising a first plate segment and a second plate segment. The first plate segment comprises at least one member for engagement with a second bone segment of the bone. The second plate segment comprises at least one slot for receiving at least one bone screw to secure a first bone segment with the second bone segment to form a corrective construct.

In an embodiment, a fixation plate is disclosed. The fixation plate comprises a first portion, a second portion, and a third portion. The first portion comprises at least one member for engagement with a second bone segment. The second portion comprises at least one slot to secure a first bone segment with the second bone segment. The third portion is coupled between the first portion and the second portion. The at least one member is positioned at an angle or an offset from the second portion and the third portion In another embodiment the at least one slot receives at least one male fixation member.

In another embodiment, the at least one male fixation member is at least one of a screw, pin, bolt, or nail.

In another embodiment, the at least one male fixation member interacts with the at least one slot based on an application of compressive force to the at least one male fixation member.

In another embodiment, the at least one slot is a compression slot.

In another embodiment, the at least one member comprises fixation means for affixing to the second bone segment.

In another embodiment, the first portion and the second portion are connected by the third portion with a hinged connection.

In another embodiment, the first portion and the second portion comprises a first thickness, and the third portion comprises a second thickness.

In another embodiment, the first portion and the second portion comprise a first material, and the third portion comprises a second material.

These and other advantages of the embodiments of the present disclosure will be apparent to those of ordinary skill in the art by reference to the following Detailed Description and accompanying drawings/figures.

DETAILED DESCRIPTION

The present disclosure described herein provides a system and method bone fixation. More specifically, a method and system for corrective bunionectomy surgery of a bone is disclosed. The present disclosure facilitates secure fixation of cut metatarsal bone sections. When carrying out bunionectomy surgery, a metatarsal bone is typically cut into a first bone segment and a second bone segment. After applying a corrective angle between the first bone segment and the second bone, a plate may be applied to the first bone segment and the second bone segment to reconnect the bone segments into a corrective construct.

Provided herein is a system and method for carrying out corrective bunionectomy surgery and bone fixation. In the various embodiments described herein and corresponding with the Figures provided herewith, a bone fixation method and system are described with respect to a metatarsal bone. A metatarsal bone is cut into a first bone segment and a second bone segment. A plate is positioned over the first bone segment and the second bone segment such that a plate portion comprising claws is positioned over the second bone segment and a plate portion comprising a compression slot for receiving a bone screw is positioned over the first bone segment. The claws are inserted into the second bone segment to attach the plate to the second bone segment. A bone screw may be screwed through the compression slot of the plate to secure the first bone segment to the plate. Tightening of the screw causes the first bone segment and the second bone segment to move towards the first bone segment and form a corrective construct. Alternatively, in place of a compression slot a non-compressive slot may be included for securing the bone segments in a fixed position or angle.

Figure 1A:
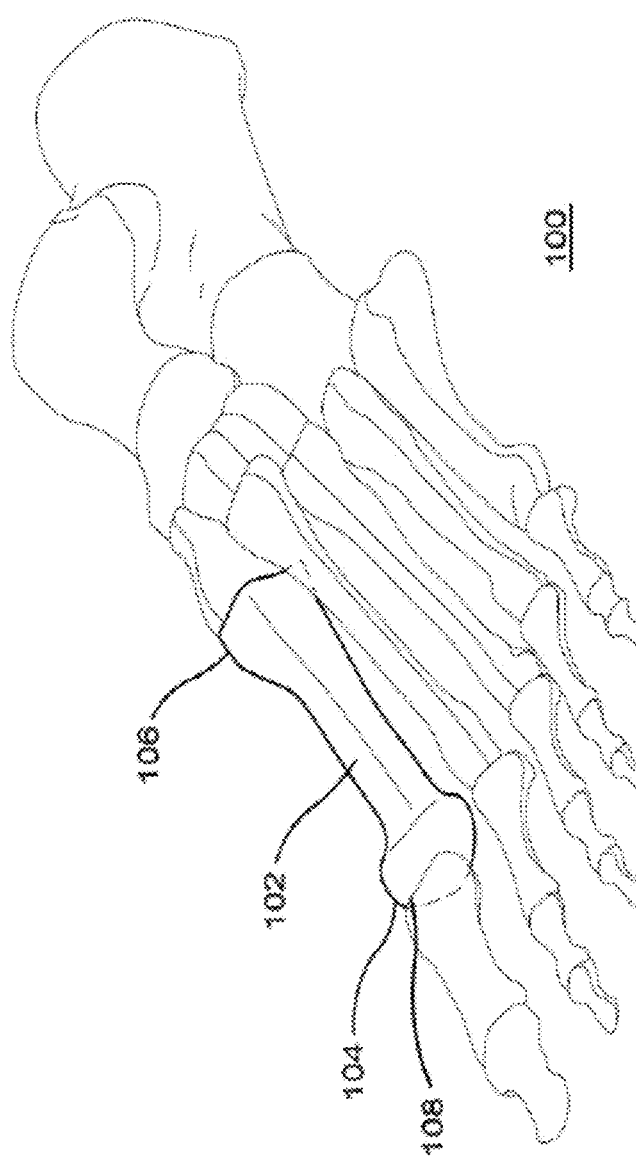
FIG. 1A illustrates a perspective view of an exemplary left foot bone structure, in accordance with an embodiment.

FIG. 1A illustrates a perspective view of an exemplary healthy left foot bone structure, in accordance with an embodiment. Left foot bone structure 100 includes a first metatarsal bone 102 and an area where bunion 104 could be located at a distal end 108 of the first metatarsal bone 102. By way of illustration and description, the following paragraphs and corresponding figures describe a system and method for corrective bunionectomy surgery and applying a bone fixation plate for the left foot. However, it is understood that the system and method may also be applied to the right foot bone structure in a similar fashion.

Figure 1B:
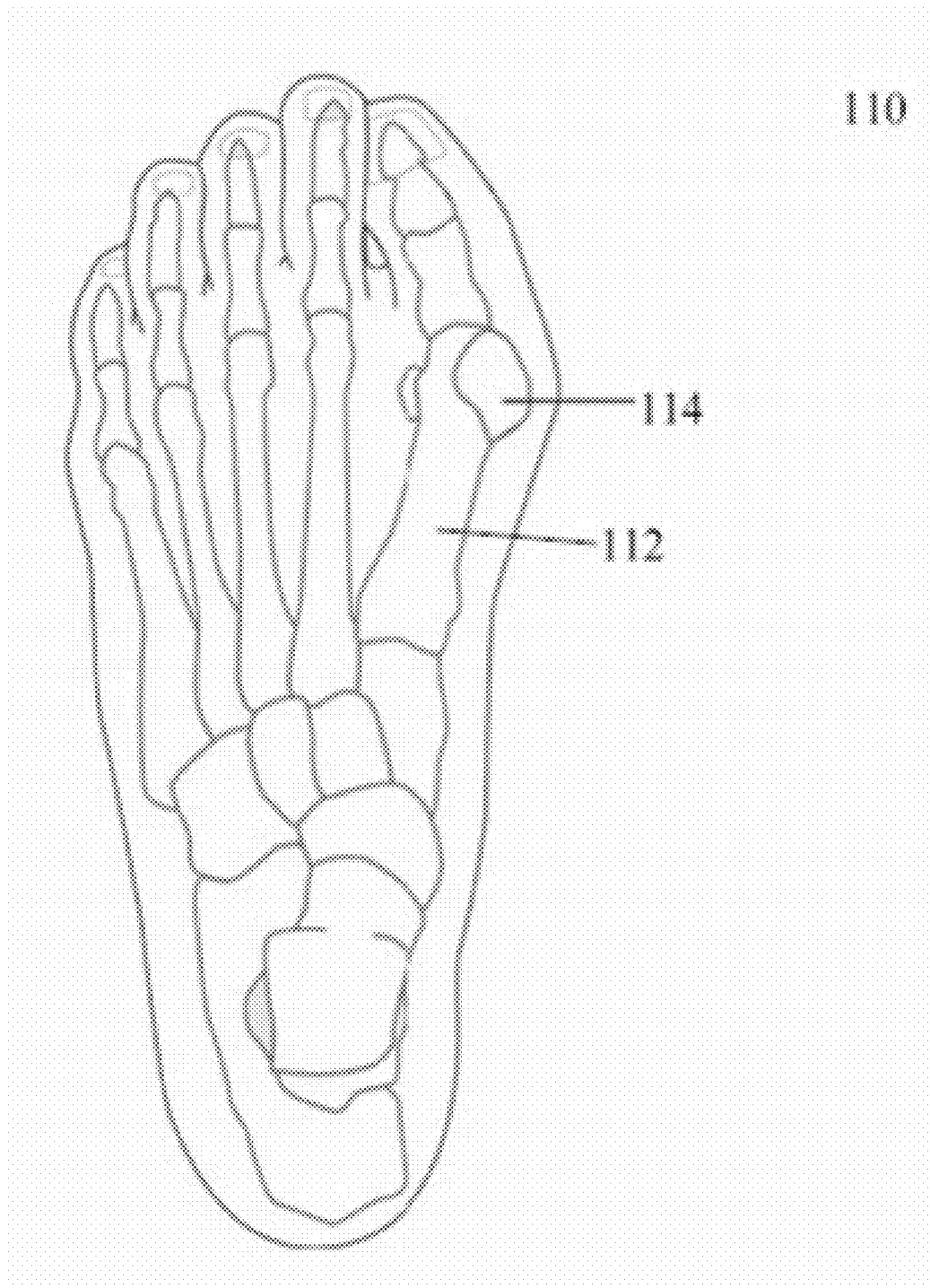
FIG. 1B illustrates a top view of an exemplary left foot bone structure, in accordance with an embodiment.

FIG. 1B illustrates a top view of an exemplary left foot bone structure, in accordance with an embodiment. Left foot bone structure 110 includes a first metatarsal bone 112, which includes a bunion 114. A bunion may also be located at a similar location for a right foot bone structure. The embodiments described herein disclose devices and methods for applying corrective bone fixation procedures to bunions. While certain embodiments described herein may be directed to bunionectomy surgery, the same embodiments may also be applied to general bone fixation procedures for corrective surgery of other bones that are located throughout the body.

Figure 1C:
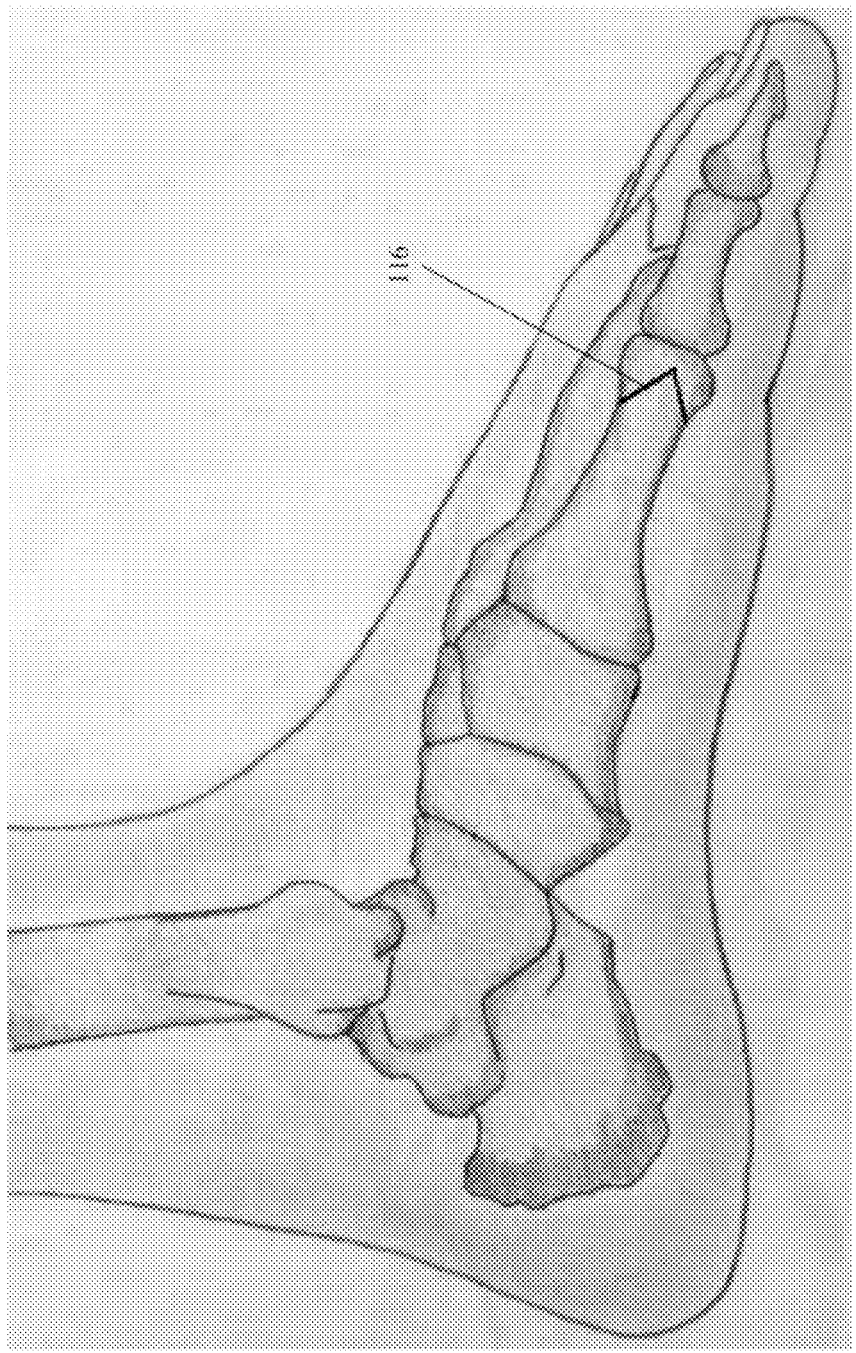
FIG. 1C illustrates an exemplary left bone structure with a chevron osteotomy for bunion correction.

FIG. 1C illustrates an exemplary left bone structure with a chevron ostetomy for bunion correction. A left foot born structure within a left foot is shown. A chevron osteotomy 116 in the form of a "V" shaped osteotomy of the first metatarsal is shown. In an embodiment, a cut into a metatarsal bone may involve a chevron osteotomy procedure. A V-shaped cut is made in the metatarsal bone near the metatarsal head. A corrective angle may then be applied to the two cut parts of the bone. While the chevron osteotomy relates to metatarsals and correction of bunions or hallux vallgus, the chevron osteotomy may be applied to other bones or joints as contemplated in accordance with the embodiments described herein.

Figure 2:
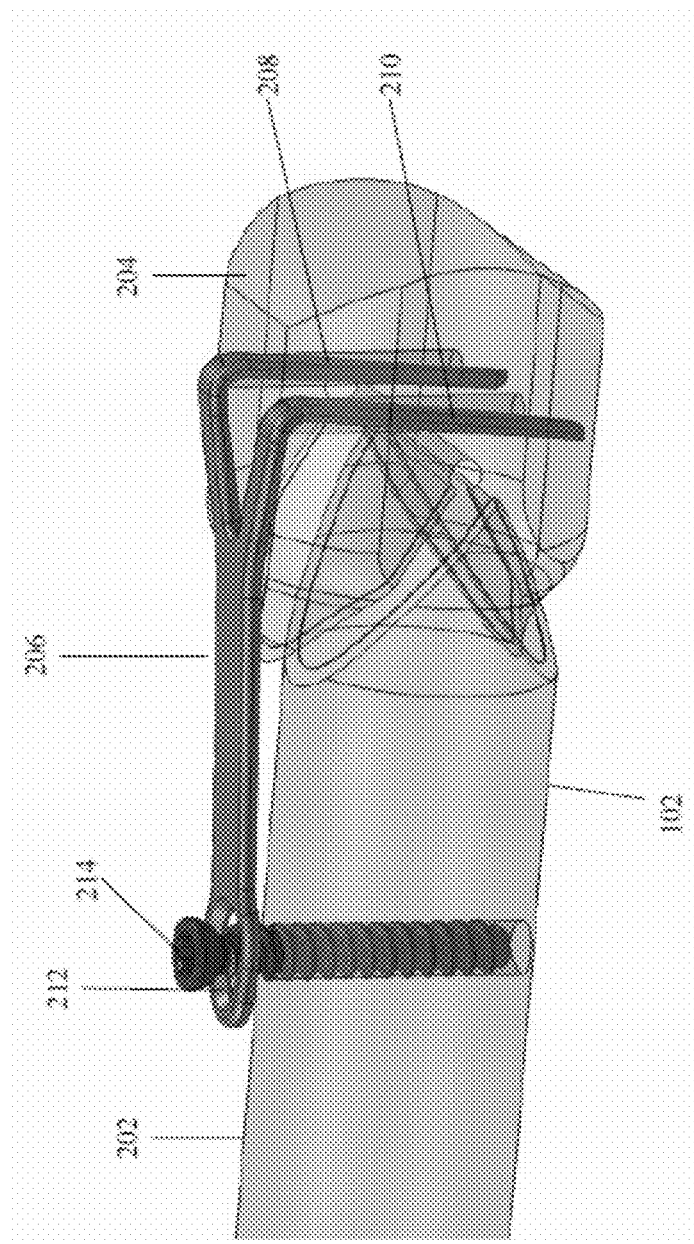
FIG. 2 illustrates a perspective view of an exemplary first metatarsal bone with plate attached, in accordance with an embodiment.

FIG. 2 illustrates a perspective view of an exemplary first metatarsal bone with plate attached, in accordance with an embodiment. Metatarsal bone 102 is shown after exposure of the bone during surgery. Metatarsal bone 102 as shown has been cut into a first bone segment 202 and a second bone segment 204. The cut in the metatarsal bone may be based on a guide that is placed over the bone. First bone segment 202 represents a proximal portion of the bone and second bone segment 204 represents a distal portion of the bone. First bone segment 202 and second bone segment 204 may be placed at a corrective position with respect to each other before first bone segment 202 and second bone segment 204 receive plate 206 which is used to rejoin first bone segment 202 and second bone segment 204 as a corrective construct. A typical shift of second bone segment 204 with respect to first bone segment 202 may be several millimeters.

Plate 206 as shown has been affixed to bone 102. Plate 206 includes two claw members 208 and 210. Each of the claw members 208 and 210 are engaged and attached within second bone segment 204. Claw members 208 and 210 may engage or attach with second bone segment 204 by receiving a downward compressive force, or downward stapling force from any device capable of applying such force, such as a compressive force device or a stapling mechanism. Claw members 208 and 210, as well as all claw members described herein, may include teeth, barbs, or some other surface irregularity for biting into or securing a bone segment to support improved fixation.

Claw members 208 and 210 may also, in an embodiment, be tines or staples. Additionally, claw members 208 and 210 may include a plurality of barbs, notches, grooves, or a nonuniform surface to facilitate attachment to the second bone segment. Each of claw members 208 and 210 is positioned at an angle or an offset from the remainder of plate 206.

Plate 206 also includes hole 212 for receiving bone screw 214. Bone screw 214 is screwed into first bone segment 202 through compression slot 212 after a pilot hole has been drilled into first bone segment 202. Bone screw 214 affixes the first bone segment 202 to plate 206. Compression slot 212 may be shaped such that as bone screw 214 is screwed into first bone segment 202, compression slot 212 supports movement of plate 206 such that second bone segment 204 and first bone segment 202 are caused to move towards each other to form a corrective bone construct.

While bone screws are shown, any male fixation member may be used in place of a bone screw. The male fixation member may be a screw, pin, bolt, or a nail. The male fixation member interacts with the compression slot to cause engagement of the at least one member with the second bone segment. The male fixation member may also comprise additional fixation structures such as barbs or surface irregularities thereon to promote attachment to the first bone segment.

Due to a shape of compression slot 212, compressive force is applied to plate 206 which causes second bone segment 204 and first bone segment 202 to move towards each other and form the corrective bone construct. Compression slot 212 includes two radii on each end, tangentially connected via linear or near linear surfaces. A chamfer is included on at least one of these edges which acts as a screw receiving recess. One of the two radii is larger and matches the head of bone screw 214, and will support a final position of bone screw 214. Bone screw 214 is inserted into the end with a smaller radius. As bone screw 214 is tightened, the chamfer is dragged and rides along the head of bone screw 214 and moves the end of the compression slow 212 having the larger radius toward the head of the bone screw 214, effectively reducing the fusion site and creating residual compressive force on the bone segments. While this description is in correspondence with FIG. 2, the description of certain elements of FIG. 2 may also be applicable to other embodiments as necessary and in accordance with one who is of ordinary skill in the art. For example, while the embodiments described herein are with respect to bones and bone segments, the embodiments may also be applied to joints or other portions of the human body requiring joining as applicable to one of ordinary skill in the art.

Furthermore, any portion of bone plate 206 may comprise a different thickness and flexibility. For example, the compression slot 212 and the tines 208 and 210 may have a first thickness or may comprise a first material and the portion of the plate 206 between the tines 208 and 210 and the compression slot 212 may have a second thickness or be comprised of a second material. The first thickness may be greater than the second thickness or less than the second thickness. The first material may be more rigid or stiff than the second material and the second material may be more flexible or malleable than the first material. Thus, any portion of bone plate 206 may be composed of different materials, different thicknesses, and different stiffness characteristics. Portions of a bone plate 206 or bone plate 206 in its entirety may comprise any biocompatible material, metal, or alloy, such as stainless steel, nitinol, and titanium. Alternatively, the bone plate or portions of the bone plate may be bioabsorbable.

While the embodiments described herein each embody different characteristics, it is understood to one of ordinary skill in the art that features of all embodiments described herein with respect to each of the individual Figures may be combined with features described with respect to other Figures of the present disclosure.

Figure 3:
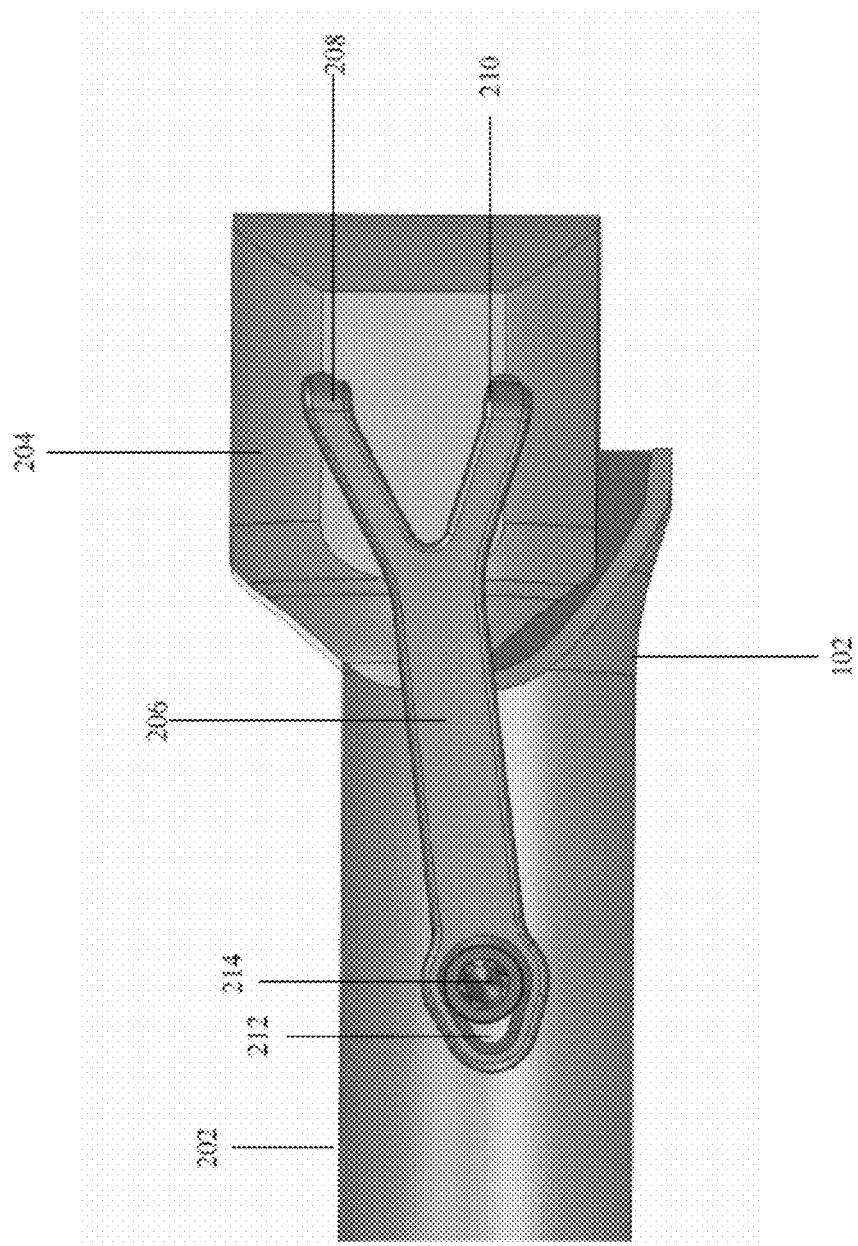
FIG. 3 illustrates a top perspective view of an exemplary first metatarsal bone with plate attached, in accordance with an embodiment.

FIG. 3 illustrates a top perspective view of an exemplary first metatarsal bone with plate attached, in accordance with an embodiment. While FIGS. 2 and 3 show a top perspective view of a left metatarsal bone with plate attached, the same principles described herein with respect to plates may be applied to plates for right metatarsal bones. The embodiment illustrated by FIG. 3 illustrates how a plate may be asymmetric. Claw members or tines of the plate may be in a coronal plane (shown vertically by FIG. 3) and bone screw 214 centralized within first bone segment 202. Claw members 208 and 210 are in an optimized location and are not off to or favoring one side or the other. This facilitates even loading of fusion surfaces to further stabilize the corrective bone construct that is formed.

Figure 4:
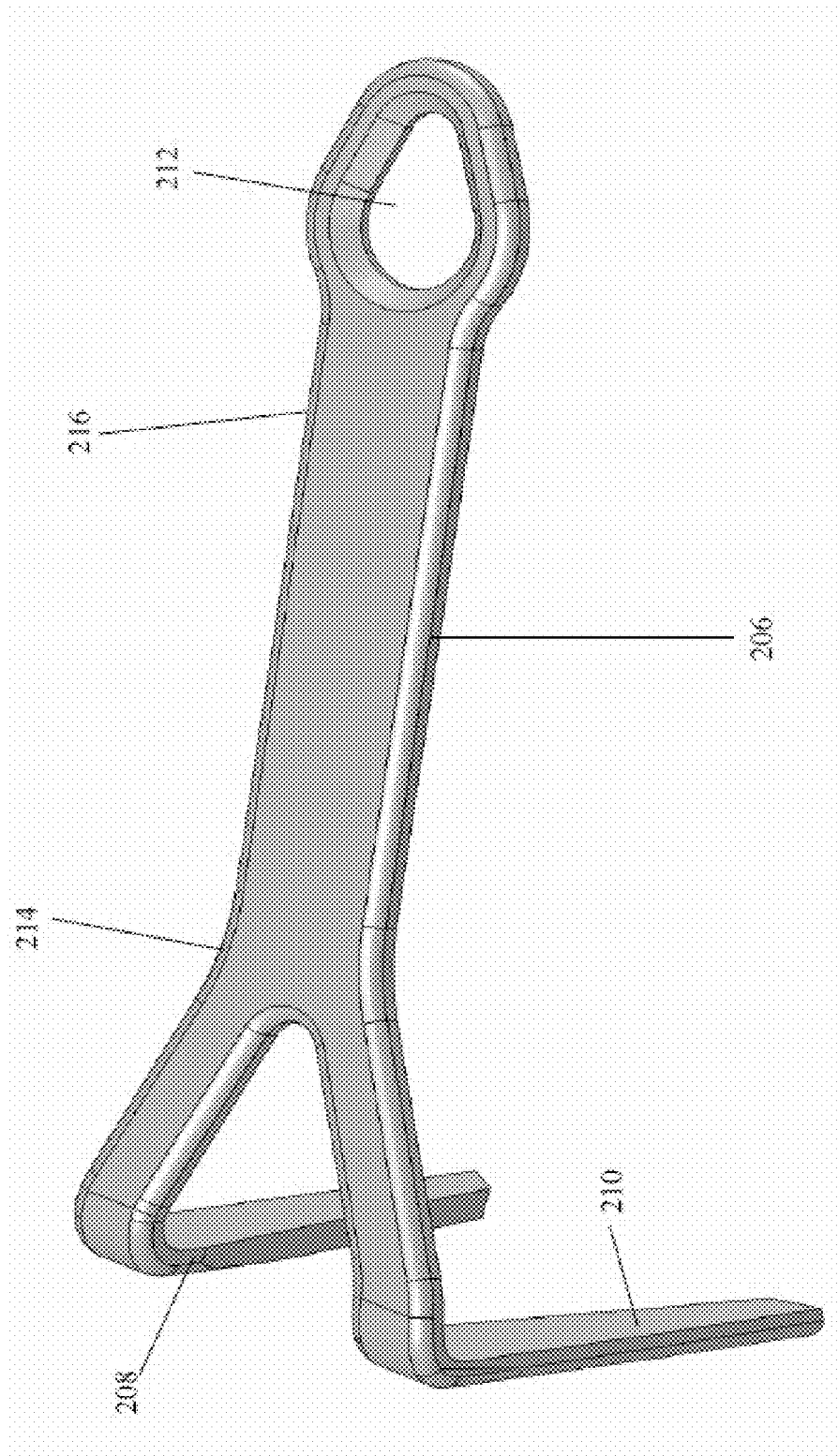
FIG. 4 illustrates a perspective view of an exemplary plate, in accordance with an embodiment.

FIG. 4 illustrates a perspective view of an exemplary plate, in accordance with an embodiment. Plate 206, as shown, includes claw members 208 and 210 for engagement and attachment to a second bone segment. Claw members 208 and 210 are a part of first plate segment 214. Claw members 208 and 210 may engage with the second bone segment by receiving a downward force that causes claw members 208 and 210 to engage. Claw members 208 and 210 form a Y-shape on first plate segment 214.

Plate 206 further includes compression slot 212 for receiving a bone screw that is screwed through a pilot hole drilled into a first bone segment. Compression slot 212 is a part of second plate segment 216. Compression slot 212 is shaped such that as a bone screw is screwed into the first bone segment, movement of the compression slot may cause plate 206 to move and facilitate the application of compression to cause the second bone segment and the first bone segment to move towards each other to form a corrective bone construct.

Figure 5:
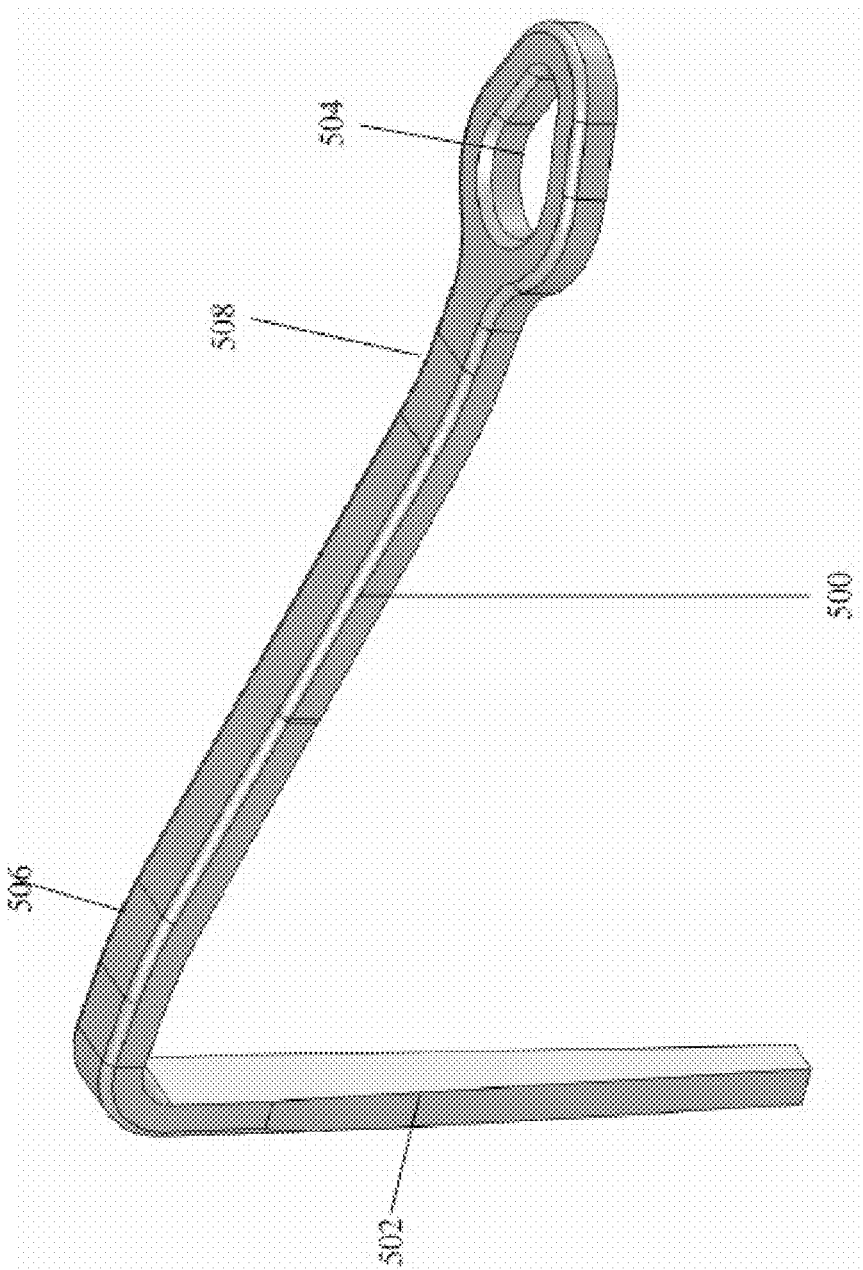
FIG. 5 illustrates a perspective view of another exemplary plate, in accordance with an embodiment.

FIG. 5 illustrates a perspective view of another exemplary plate, in accordance with an embodiment. Plate 500, as shown, includes a single claw member 502 for engagement and attachment to a second bone segment. Claw 502 is a part of first plate segment 506. Plate 500 further includes a hole 504 for receiving a bone screw that is screwed through a pilot hole drilled into a first bone segment. Compression slot 504 is a part of second plate segment 508. Compression slot 504 is shaped such that as a bone screw is screwed into the first bone segment, the bone screw may move and facilitate the application of compression to cause the second bone segment and the first bone segment to move towards each other to form a corrective bone construct.

Figure 6:
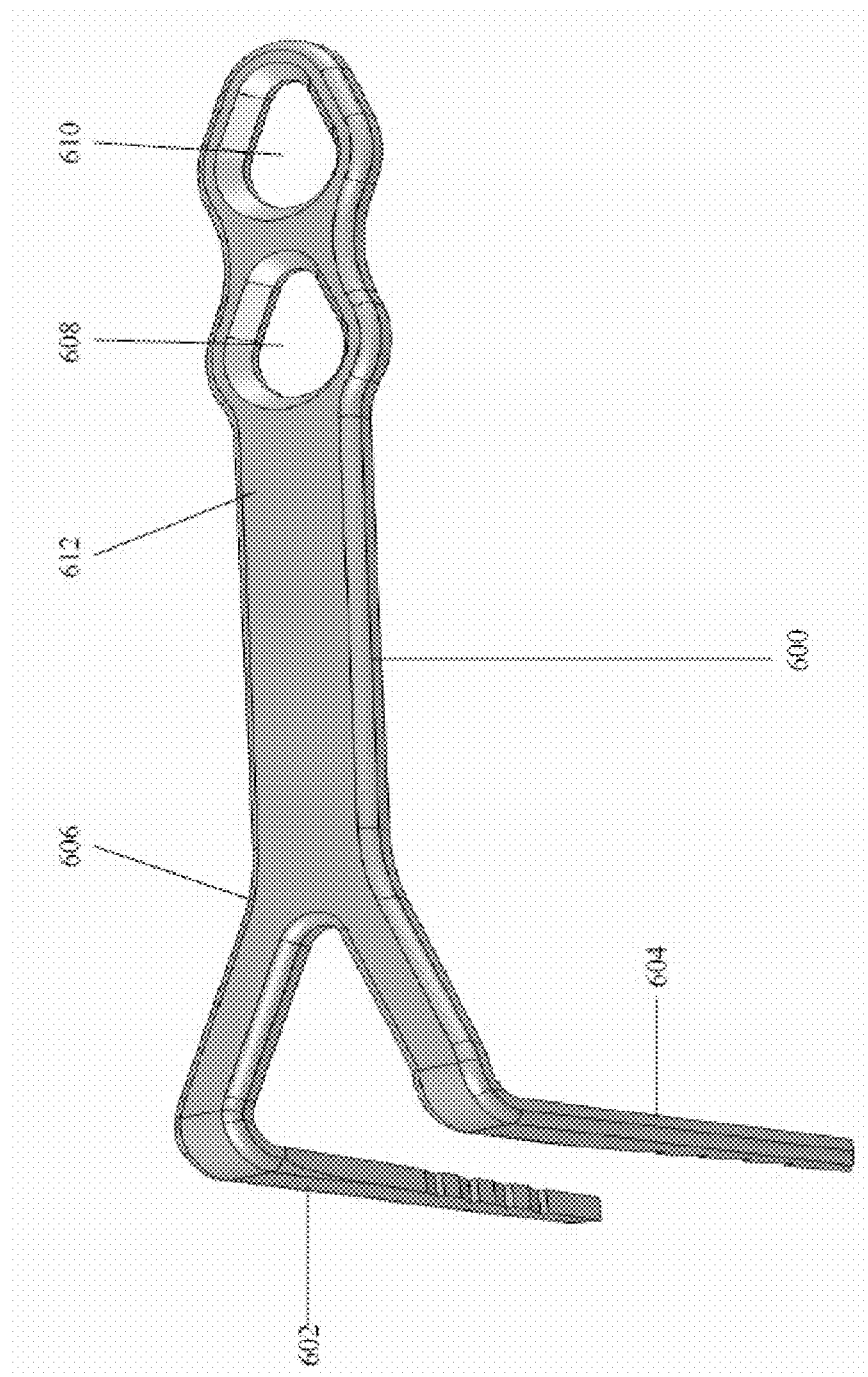
FIG. 6 illustrates a perspective view of yet another exemplary plate, in accordance with an embodiment.

FIG. 6 illustrates a perspective view of yet another exemplary plate, in accordance with an embodiment. Plate 600, as shown, includes two claw members 602 and 604. Claw members 602 and 604 are a part of first plate segment 606, and each of claw members 602 and 604 include grooves for affixing to a second bone segment during implantation. Claw members 602 and 604 form a Y shape on first plate segment 606.

Plate 600 further includes two compression slots 608 and 610. Holes 608 and 610 are a part of second plate segment 612. Each of compression slots 608 and 610 are shaped to receive bone screws that may be screwed into a first bone segment through pilot holes drilled into the first bone segment. The compression slots 608 and 610 are further shaped to facilitate movement of the compression slots 608 and 610 and the plate 600 such that during screwing of the bone screws, an application of compression causes the second bone segment and the first bone segment to move towards each other to form a corrective bone construct. The usage of two compression slots 608 and 610 prevents rotation of plate 600 and/or the first bone segment and the second bone segment and provides extra stability and leverage to the corrective bone construct once the bone screws are tightened.

Figure 7:
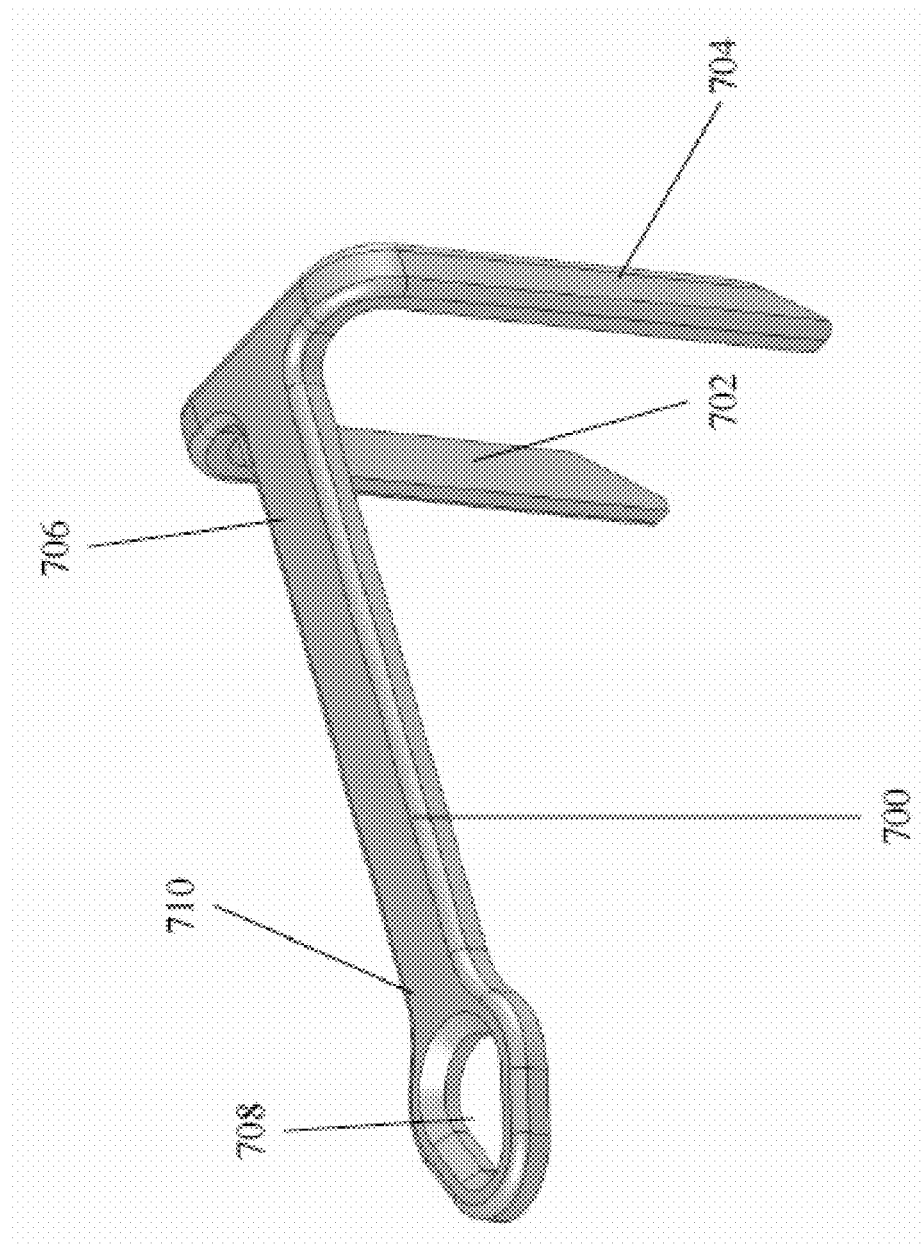
FIG. 7 illustrates a perspective view of yet another exemplary plate, in accordance with an embodiment.

FIG. 7 illustrates a perspective view of yet another exemplary plate, in accordance with an embodiment. plate 700, as shown, includes two claw members 702 and 704.

Claw members 702 and 704 are a part of first plate segment 706. Claw members 702 and 704 protrude downwards from first plate segment 706 and are configured for engagement and attachment to a second bone segment.

Plate 700 further includes a compression slot 708 for receiving a bone screw that is screwed through a pilot hole drilled into a first bone segment. Compression slot 708 is a part of second plate segment 710. Compression slot 708 is shaped such that as a bone screw is screwed into the first bone segment, the compression slot 708 may move causing the plate 700 to move and facilitating the application of compression to cause the second bone segment and the first bone segment to move towards each other to form a corrective bone construct.

Figure 8:
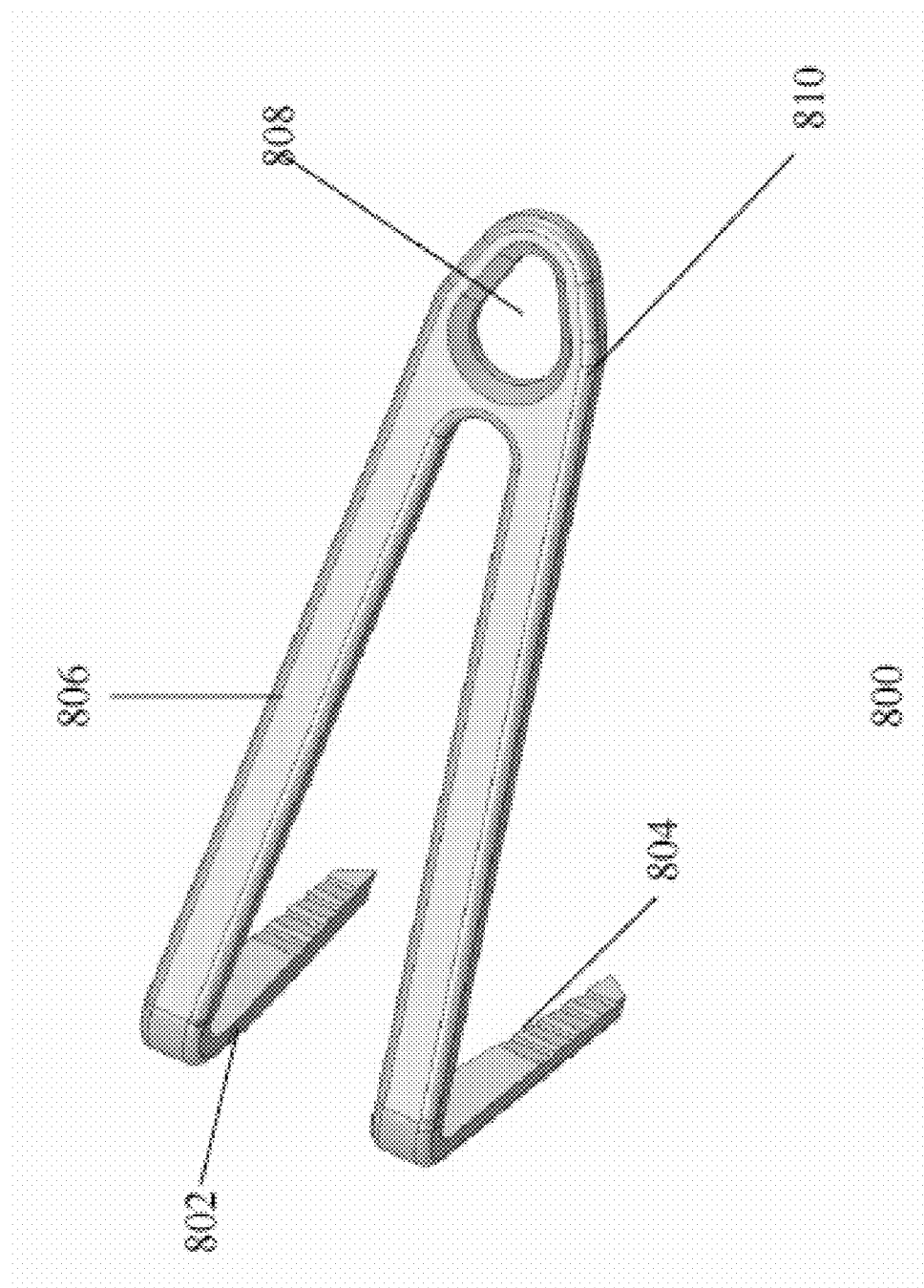
FIG. 8 illustrates a perspective view of yet another exemplary plate, in accordance with an embodiment.

FIG. 8 illustrates a perspective view of yet another exemplary plate, in accordance with an embodiment. Plate 800, as shown, includes two elongated claw members 802 and 804. Claw members 802 and 804 are a part of first plate segment 806. Claw members 802 and 804 form a Y-shape on first plate segment 806 and each of claw members 802 and 804 include grooves for affixing to a second bone segment during implantation.

Plate 800 further includes a compression slot 808 for receiving a bone screw that is screwed through a pilot hole drilled into a first bone segment. Compression slot 808 is a part of second plate segment 810. Compression slot 808 is shaped such that as a bone screw is screwed into the first bone segment, the compression slot 808 may move causing movement of the plate 800 and facilitating the application of compression to cause the second bone segment and the first bone segment to move towards each other to form a corrective bone construct.

Figure 9:
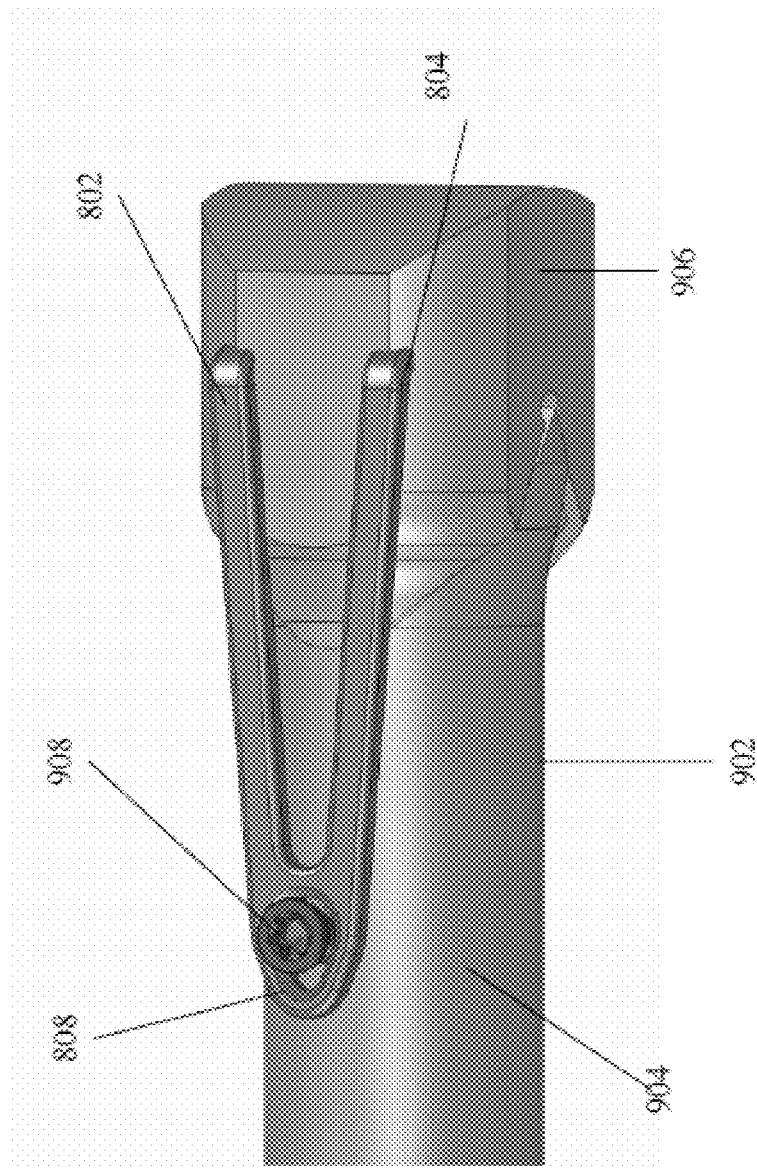
FIG. 9 illustrates a perspective view of an exemplary plate, affixed to a first metatarsal bone, in accordance with an embodiment.

FIG. 9 illustrates a perspective view of an exemplary plate, affixed to a first metatarsal bone, in accordance with an embodiment. Metatarsal bone 902 is shown after exposure of the bone during surgery. Metatarsal bone 902 as shown has been cut into a first bone segment 904 and a second bone segment 906. First bone segment 904 represents a proximal portion of the bone and second bone segment 906 represents a distal portion of the bone. First bone segment 904 and second bone segment 906 may be placed at a corrective angle with respect to each other before first bone segment 904 and second bone segment 906 receive plate 800 which is used to rejoin first bone segment 904 and second bone segment 906 as a corrective construct.

Claw members 802 and 804 of plate 800, as shown, have been attached to second bone segment 906. Claw members 802 and 804 may be attached to second bone segment 906 by receiving a downward compressive force, or downward stapling force from any device capable of applying such force.

Plate 800 also includes hole 808 for receiving bone screw 908. Bone screw 908 is screwed into first bone segment 904 through compression slot 808 after a pilot hole has been drilled into first bone segment 904. Bone screw 908 affixes the first bone segment 904 to plate 800. Compression slot 808 may be shaped such that as bone screw 908 is screwed into first bone segment 904, compression slot 808 supports movement of plate 800 such that second bone segment 906 and first bone segment 904 are caused to move towards each other to form a corrective bone construct.

Figure 10:
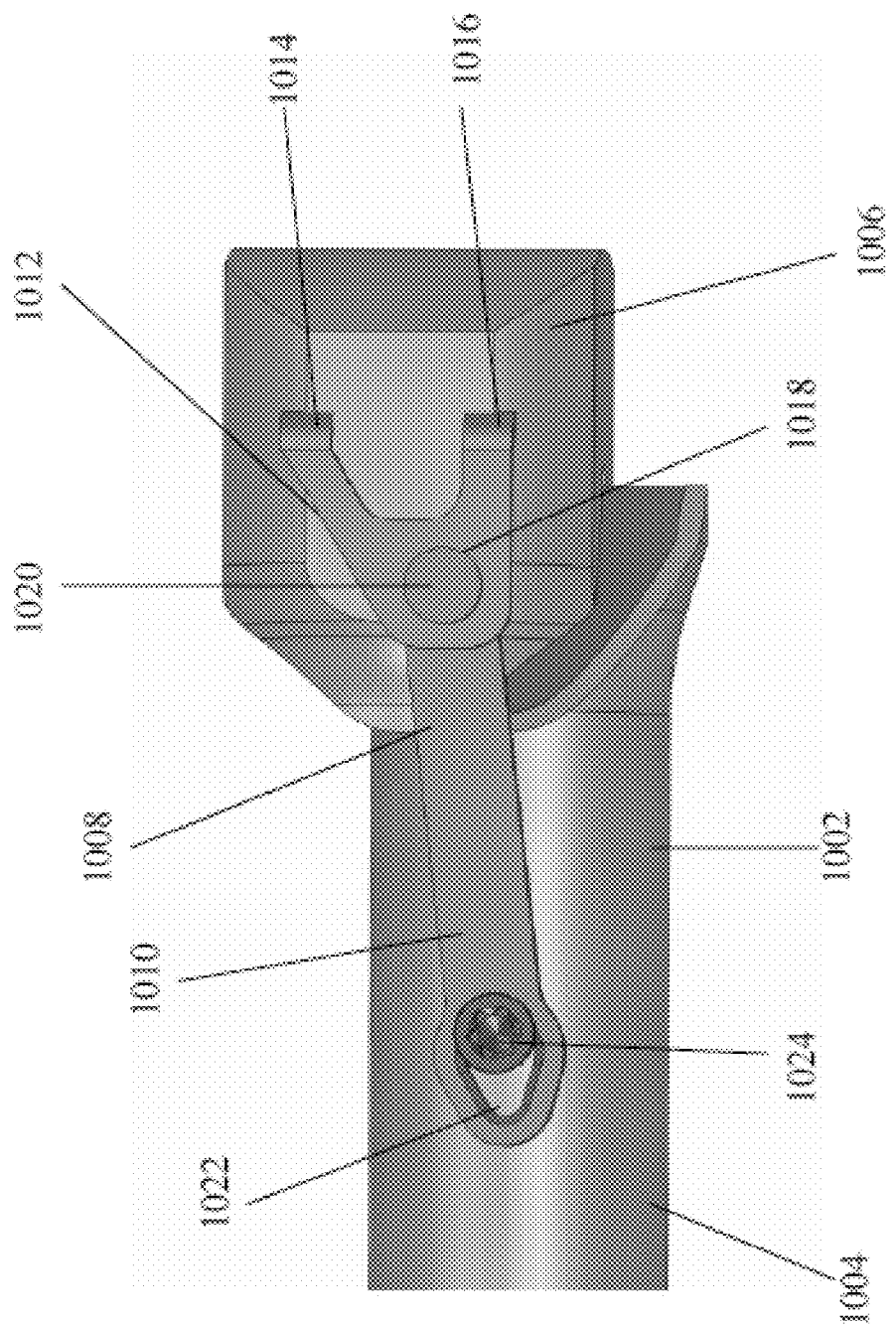
FIG. 10 illustrates a perspective view of an exemplary asymmetrical plate, affixed to a first metatarsal bone, in accordance with an embodiment.

FIG. 10 illustrates a perspective view of an exemplary plate, affixed to a first metatarsal bone, in accordance with an embodiment. The plate shown is articulating and includes a first plate segment 1010, and a second plate segment 1012, where first plate segment 1010 represents a proximal section, and second plate segment 1012 represents a distal section. Second plate section 1012 can articulate to accommodate various bone offset distances, in order to set a correction angle for two bone segments. Metatarsal bone 1002 is shown after exposure of the bone during surgery. Metatarsal bone 1002 as shown has been cut into a first bone segment 1004 and a second bone segment 1006. First bone segment 1004 represents a proximal portion of the bone and second bone segment 1006 represents a distal portion of the bone. First bone segment 1004 and second bone segment 1006 may be placed at a corrective offset or angle with respect to each other before first bone segment 1004 and second bone segment 1006 receive plate 1008 which is used to rejoin first bone segment 1004 and second bone segment 1006 as a corrective construct.

Plate 1008 includes a first plate segment 1010 and a second plate segment 1012. Claw members 1014 and 1016 may be attached to second bone segment 1006 by receiving a downward compressive force, or downward stapling force from any device capable of applying such force. Second plate segment 1012 includes boss hole 1018 for coupling with boss 1020 of first plate segment 1010. When boss 1020 and boss hole 1018 are mated, this facilitates movement of first plate segment 1010 with respect to second plate segment 1012. First plate segment 1010 also includes hole 1022 for receiving bone screw 1024. Bone screw 1024 is screwed into first bone segment 1004 through hole 1022 after a pilot hole has been drilled into first bone segment 1004. Bone screw 1024 affixes the first bone segment 1004 to plate 1008. Hole 1022 may be shaped such that as bone screw 1024 is screwed into first bone segment 1004, hole 1022 supports movement of plate 1008 such that second bone segment 1006 and first bone segment 1004 are caused to move towards each other to form a corrective bone construct.

Figure 11:
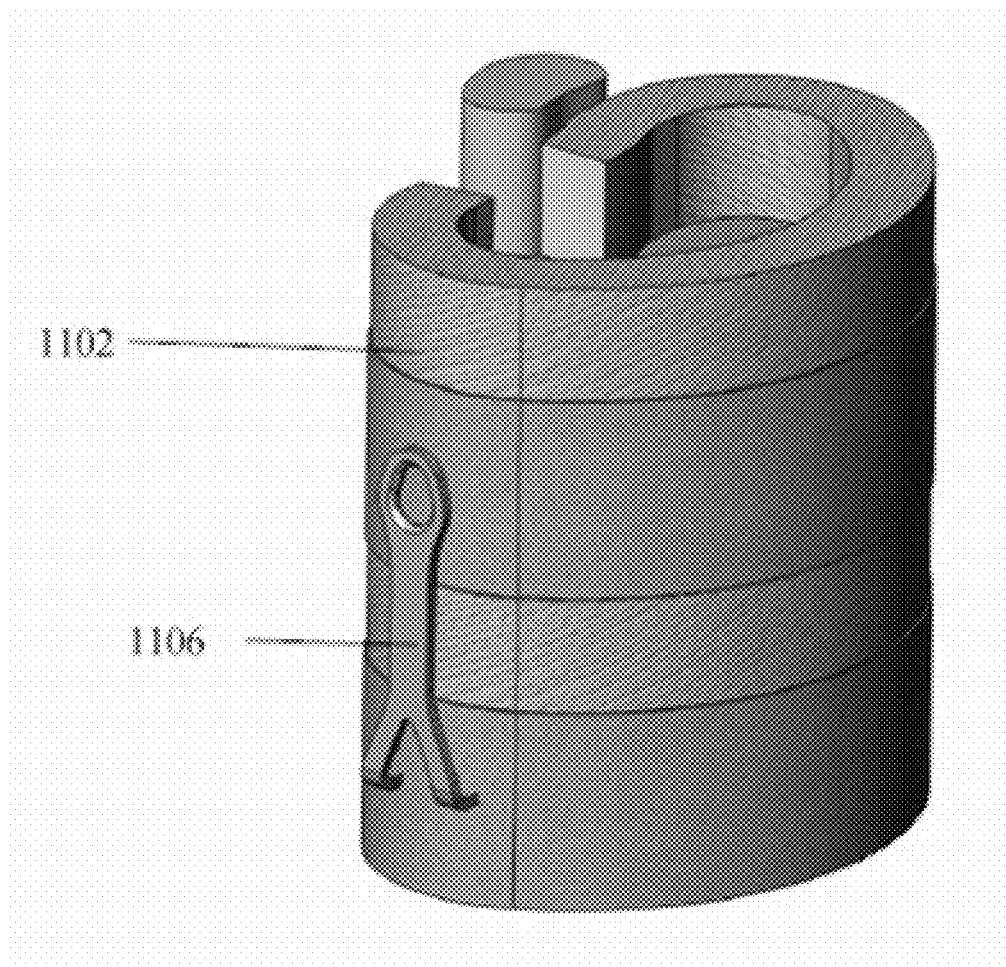
FIG. 11 illustrates a perspective view of an exemplary plate, affixed to vertebral bones, in accordance with an embodiment.

FIG. 11 illustrates a perspective view of an exemplary plate, affixed to vertebral bones, in accordance with an embodiment. Plate 1106, which is similar to plate 206 discussed above and shown in FIG. 2, is shown and affixed to lumbar vertebrae 1102. In accordance with an embodiment, plate 1106 and any of the plates described in the present disclosure, may be adapted or configured to affix to vertebral bones such as the lumbar vertebrae. Thus, a corrective bone construct of the lumbar vertebrae or other vertebral bones may be formed by using plate 1106, when a bone screw is used to fasten plate 1106, which applies compressive force and causes the lumbar vertebrae to move towards each other.

Figure 12:
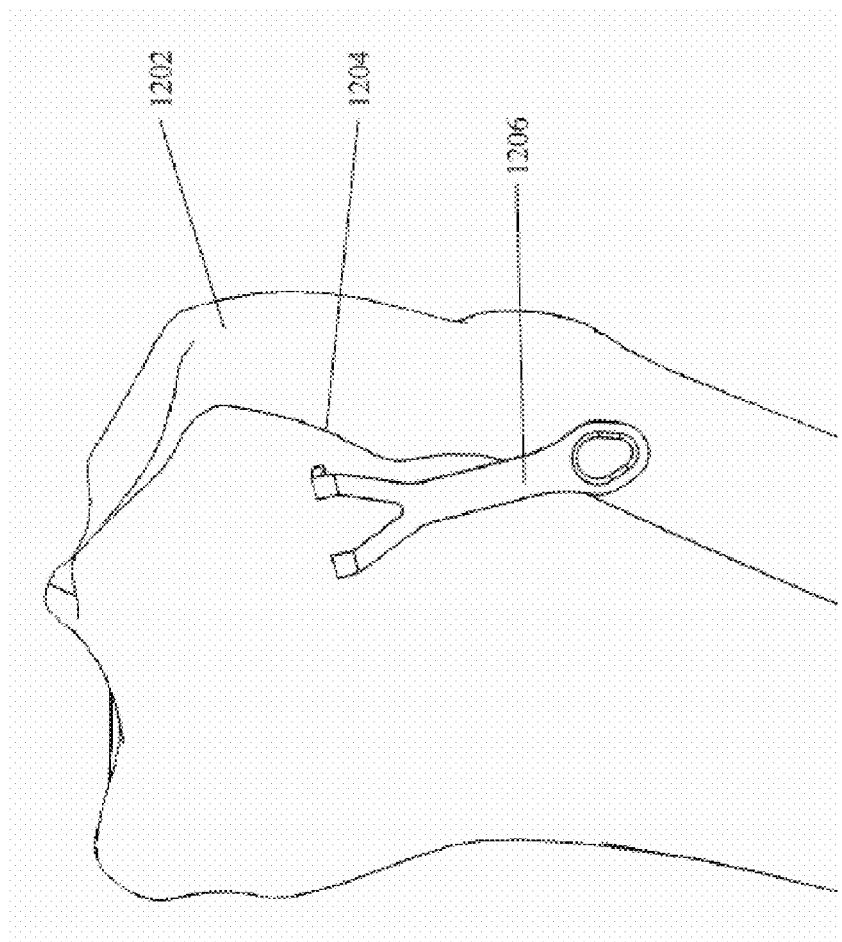
FIG. 12 illustrates a perspective view of an exemplary plate, affixed to a fractured long bone, in accordance with an embodiment.

FIG. 12 illustrates a perspective view of an exemplary plate, affixed to a fractured long bone, in accordance with an embodiment. Plate 1206, which is similar to plate 206 discussed above and shown in FIG. 2, is shown and affixed to a long bone 1202 having a fracture 1204. In accordance with an embodiment, plate 1206 and any of the plates described in the present disclosure, may be adapted or configured to affix to a long bone which has suffered from a fracture. Thus, a corrective bone construct of a fractured long bone may be formed using plate 1206, when a bone screw is used to fasten plate 1206, which applies compressive force and causes the two sections of the bone separated by the fracture to move towards each other.

Figure 13:
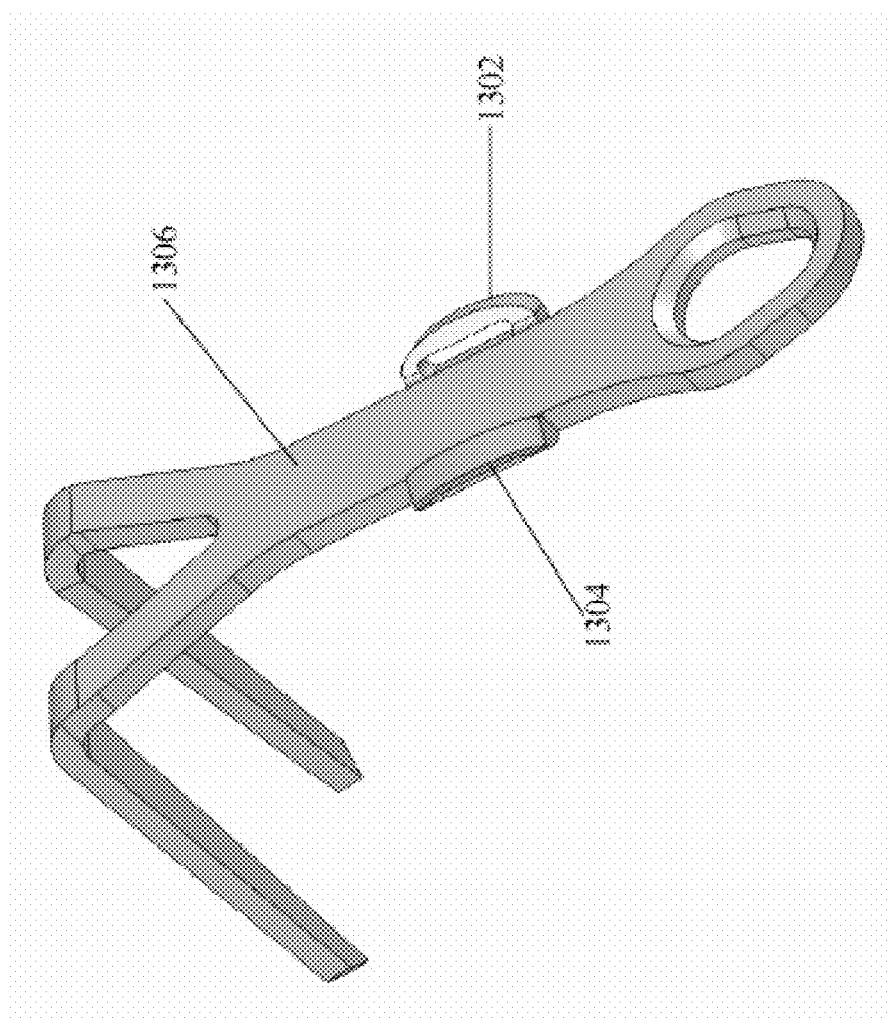
FIG. 13 illustrates an exemplary plate, including eyelets for suture anchoring, in accordance with an embodiment.

FIG. 13 illustrates an exemplary plate, including eyelets for suture anchoring, in accordance with an embodiment. Plate 1306, which is similar to plate 206 discussed above and shown in FIG. 2, additionally includes eyelets for anchoring to sutures. In accordance with an embodiment, plate 1306 may not only anchor to bone segments, but may also anchor to sutures via eyelets 1302 and 1304. Thus, a corrective bone construct may be formed using plate 1306, when a bone screw is used to fasten plate 1306, which applies compressive force and causes two bone segments to move towards each other. Additionally, eyelets 1302 and 1304 facilitate attachment or anchoring to sutures in order to secure soft tissue, such as, for example, tendons, ligaments or muscle to bone.

Figure 14:
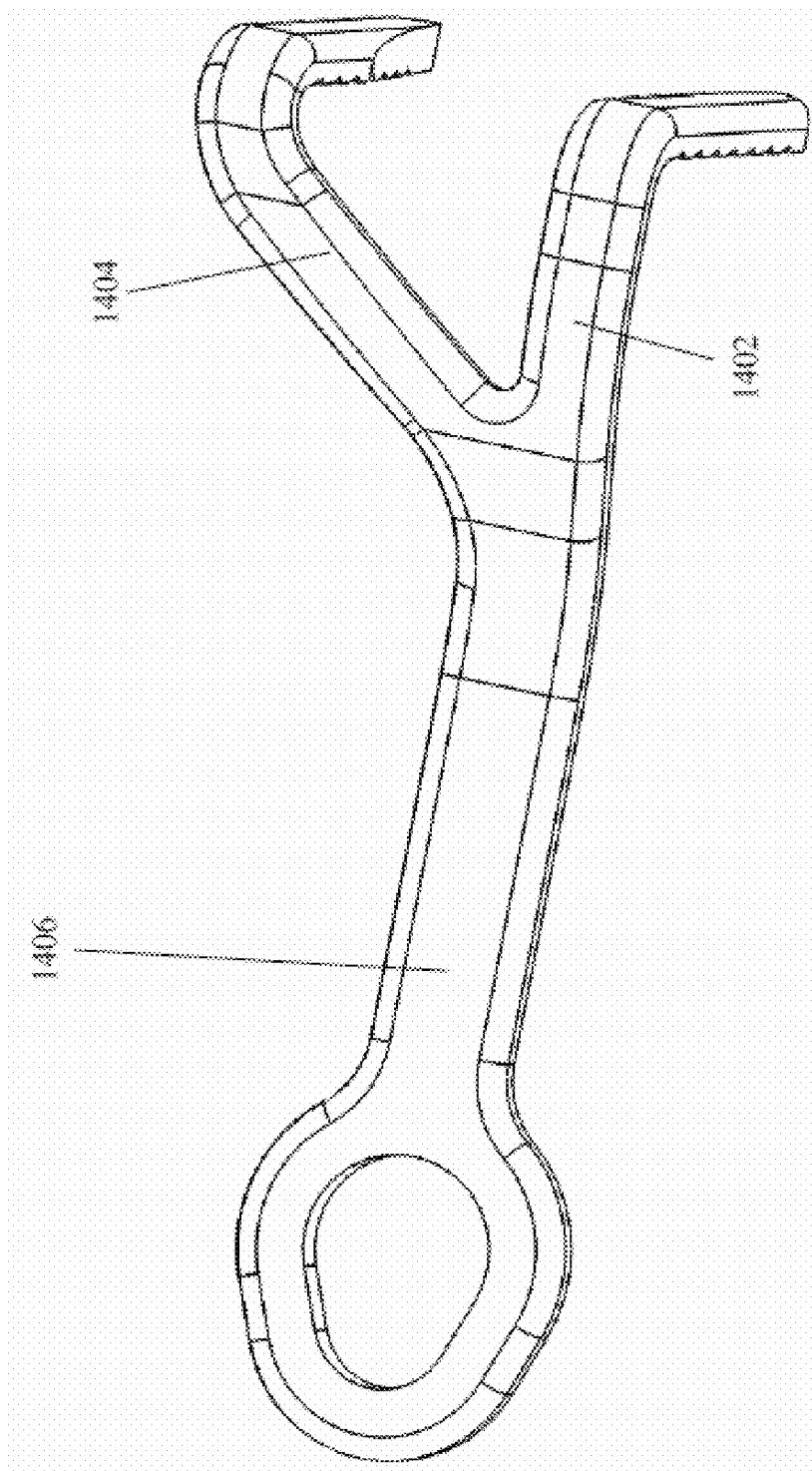
FIG. 14 illustrates an exemplary plate that is asymmetric, in accordance with an embodiment.

FIG. 14 illustrates an exemplary plate that is asymmetric, in accordance with an embodiment. Plate 1406 operates functionally in a fashion similar to that of plate 206 described above and shown in FIG. 2. Plate 1406 includes two members 1402 and 1404, which are asymmetrical. More specifically, member 1404 represents a canted member and member 1402 is parallel and in line with the remainder of plate 1406. In order to form a plate such as plate 1406, a symmetrically tined plate or plate with two symmetries may be canted. Additionally, the members may be aligned in a coronal plane with a corrective shift built into the plate.

Figure 15:
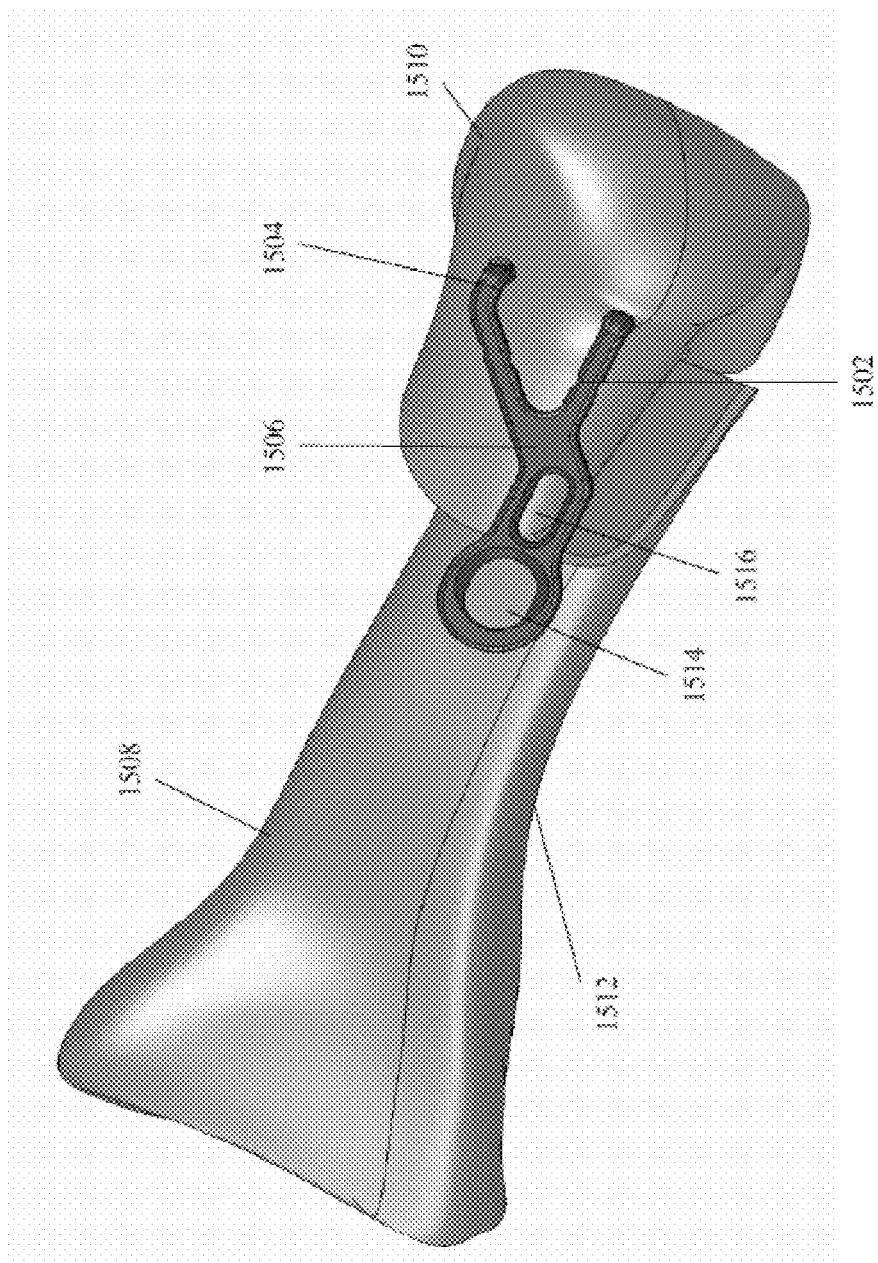
FIG. 15 illustrates an exemplary plate placed in situ in a bone, in accordance with an embodiment.

FIG. 15 illustrates an exemplary plate placed in situ in a bone, in accordance with an embodiment. Plate 1506 is asymmetric and operates functionally in a fashion similar to that of plate 206 described above and, shown in FIG. 2. Plate 1506 includes two members 1502 and 1504, which are asymmetrical. Member 1504 represents a canted member and member 1502 is parallel to the remainder of plate 1506. Plate 1506 is shown in situ within bone 1508, whereas members 1502 and 1504 are implanted in bone segment 1510. Bone segment 1512 will be attached to plate 1506 by a screw through compression slot 1514. Plate 1506 further includes an additional slot 1516 for receiving additional screws should additional stability be required.

Figure 16:
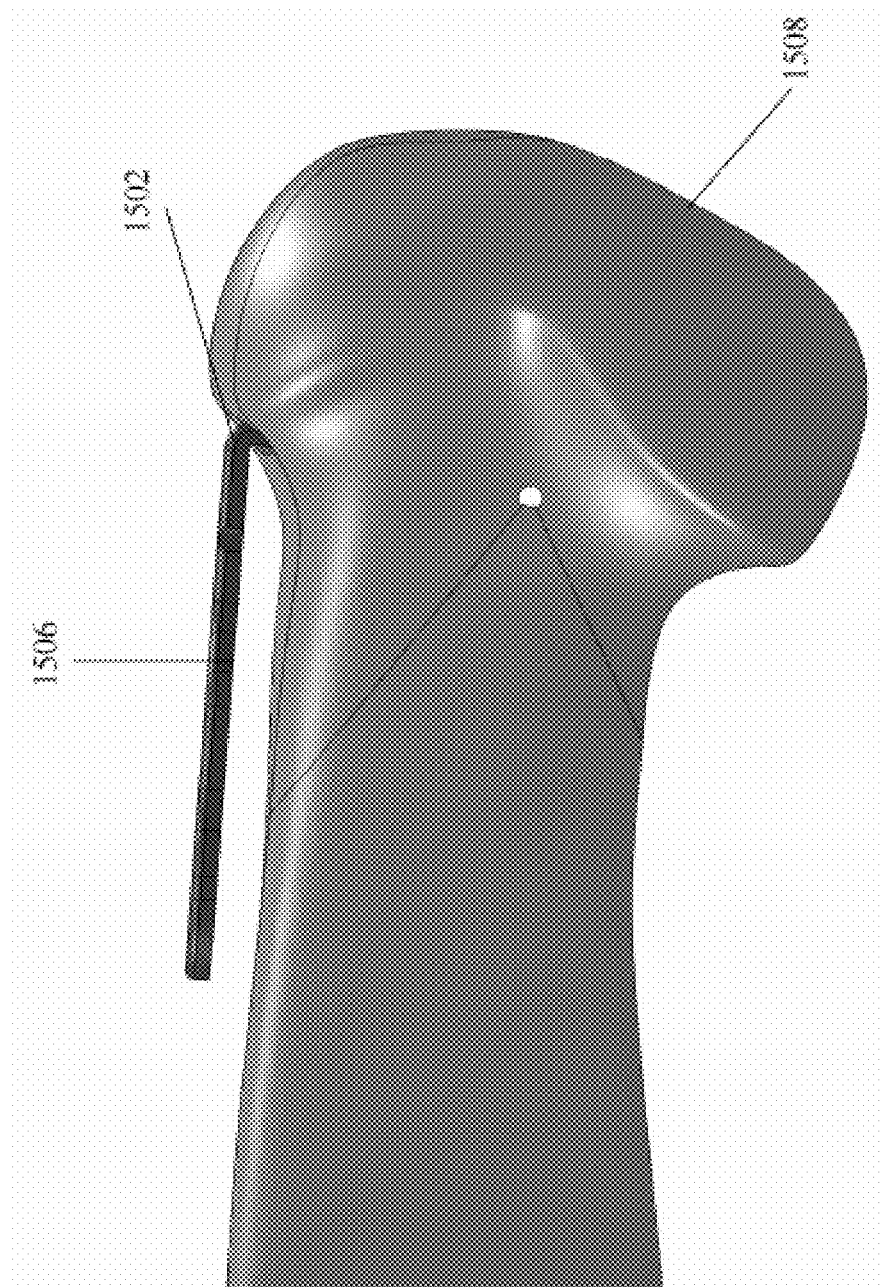
FIG. 16 illustrates a medial view of an exemplary plate placed in situ in a bone, in accordance with an embodiment.

FIG. 16 illustrates a medial view of an exemplary plate placed in situ in a bone, in accordance with an embodiment. FIG. 16 shows plate 1506 as also shown in FIG. 15, in situ in bone 1508. Member 1502 of plate 1506 is displayed as attached to bone 1508 to show the configuration of plate 1506 with respect to bone 1508.

Figure 17:
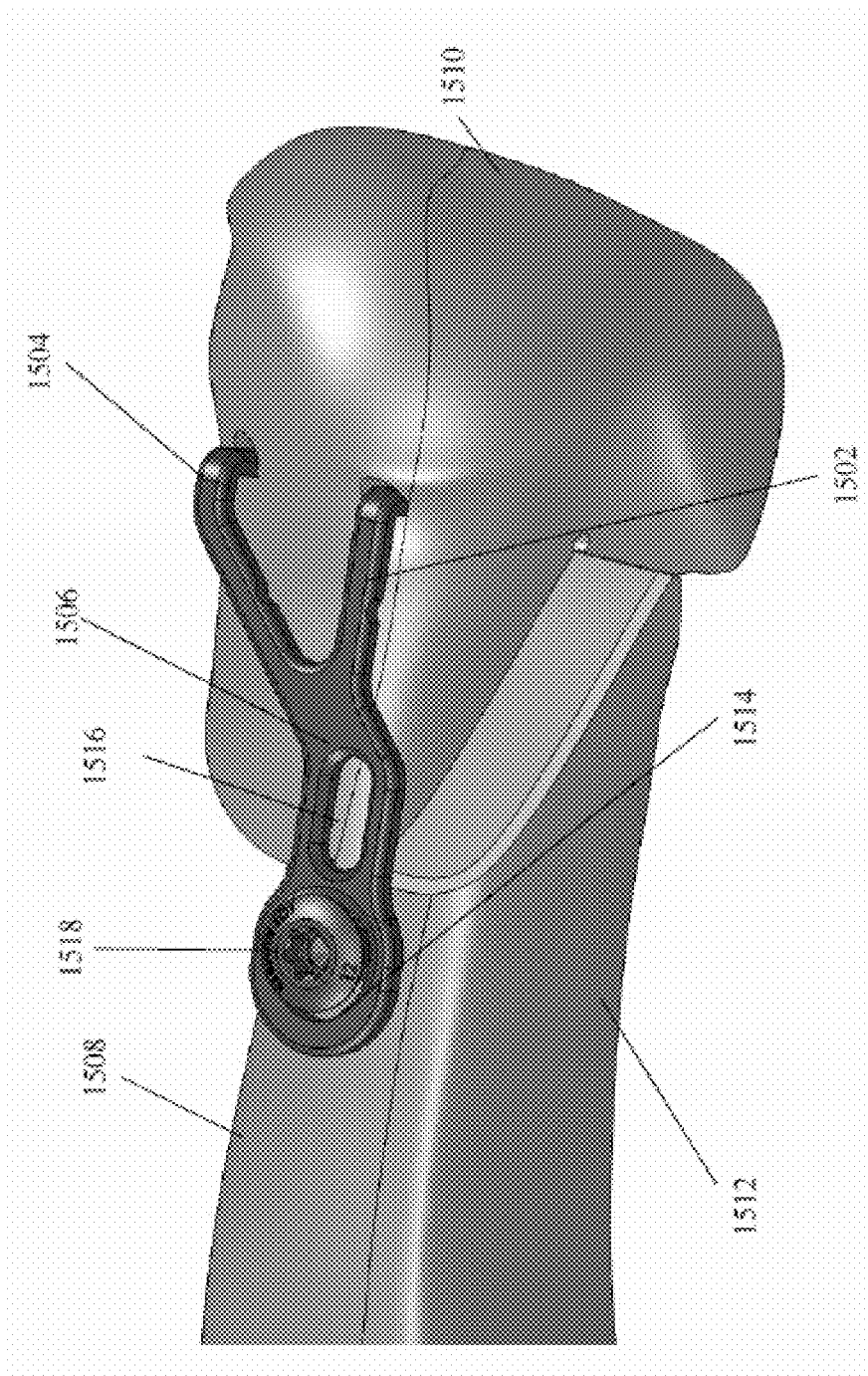
FIG. 17 illustrates an exemplary plate placed in situ in a bone with a screw applied, in accordance with an embodiment.

FIG. 17 illustrates an exemplary plate placed in situ in a bone with a screw applied, in accordance with an embodiment. FIG. 17 illustrates plate 1506 attached to bone segments 1510 and 1512. As shown in FIG. 17, members 1502 and 1504 are attached to bone segment 1510. Bone screw 1518 is shown as screwed into bone segment 1512 through compression slot 1514. Tightening or screwing of bone screw 1518 into bone segment 1512, causes compressive force to be applied to cause bone segments 1510 and 1512 to move towards each other to form a corrective construct.

Figure 18:
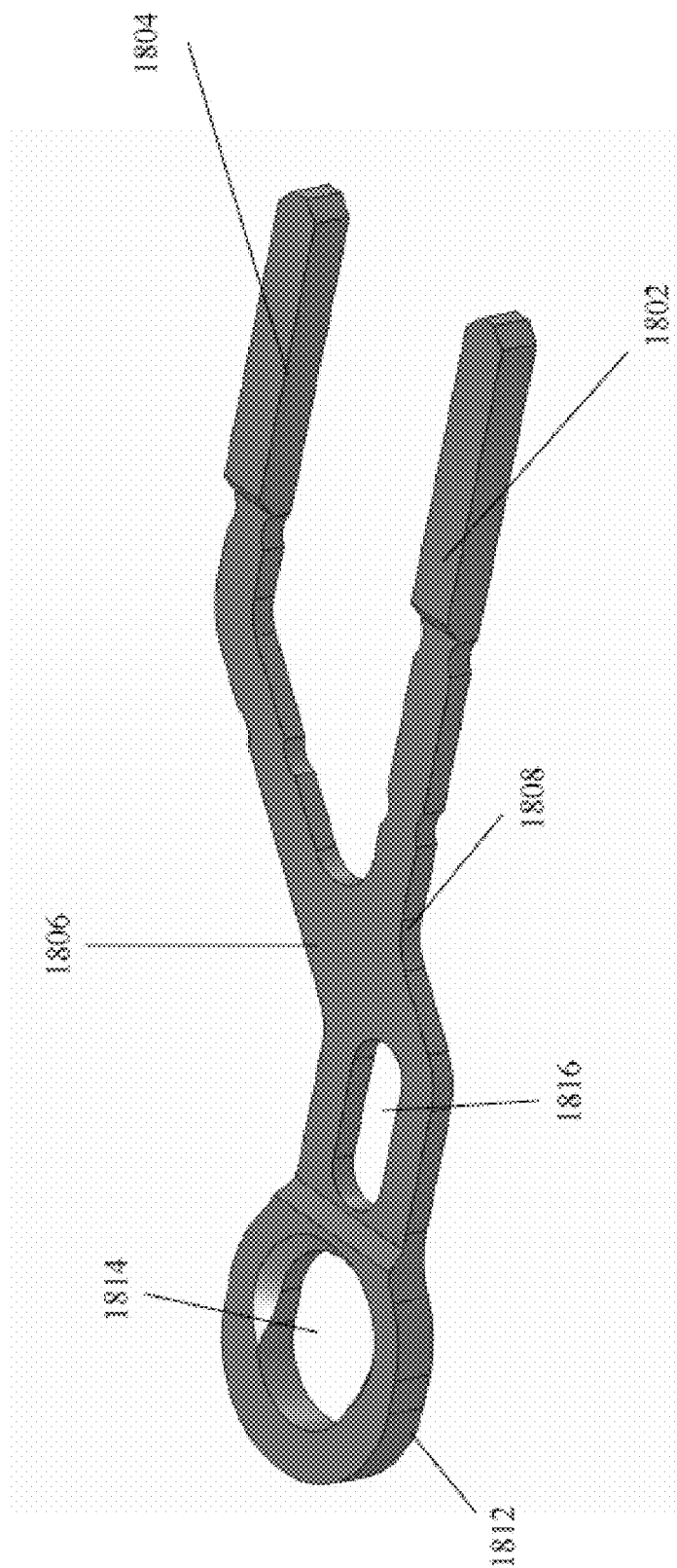
FIG. 18 illustrates an exemplary plate that is prebent with multiple thicknesses, in accordance with an embodiment.

FIG. 18 illustrates an exemplary plate that is prebent with multiple thicknesses, in accordance with an embodiment. Plate 1806 as shown operates functionally in a fashion similar to that of plate 206 described above and shown in FIG. 2. Members 1802 and 1804 as shown are flat members for insertion into a bone segment and attachment to a bone segment. Members 1802 and 1804 are parallel to plate 1806. Additionally, members 1802 and 1804 are of a differing thickness than a middle portion 1808 of plate 1806. Similarly, a compression slot section 1812 of plate 1806, which includes a compression slot 1814, is of a different thickness than middle portion 1808 of plate 1806. Members 1802 and 1804, middle section 1808, and compression slot section 1812 may all be of differing thicknesses. For example, members 1802 and 1804 may each be 1 mm thick and compression slot section 1812 may also be 1 mm thick, while middle section 1808 and the remainder of plate 1806 is a different, thinner thickness to provide improved flexibility. Compression slot 1814 supports the insertion of a bone screw for attachment of plate 1806 to a bone segment. Plate 1806 further includes an additional slot 1816 for receiving additional screws should additional stability be required. Middle section 1808 may furthermore be flexible and bend in order to adapt to joining bone segments that plate 1806 is attached to.

Figure 19:
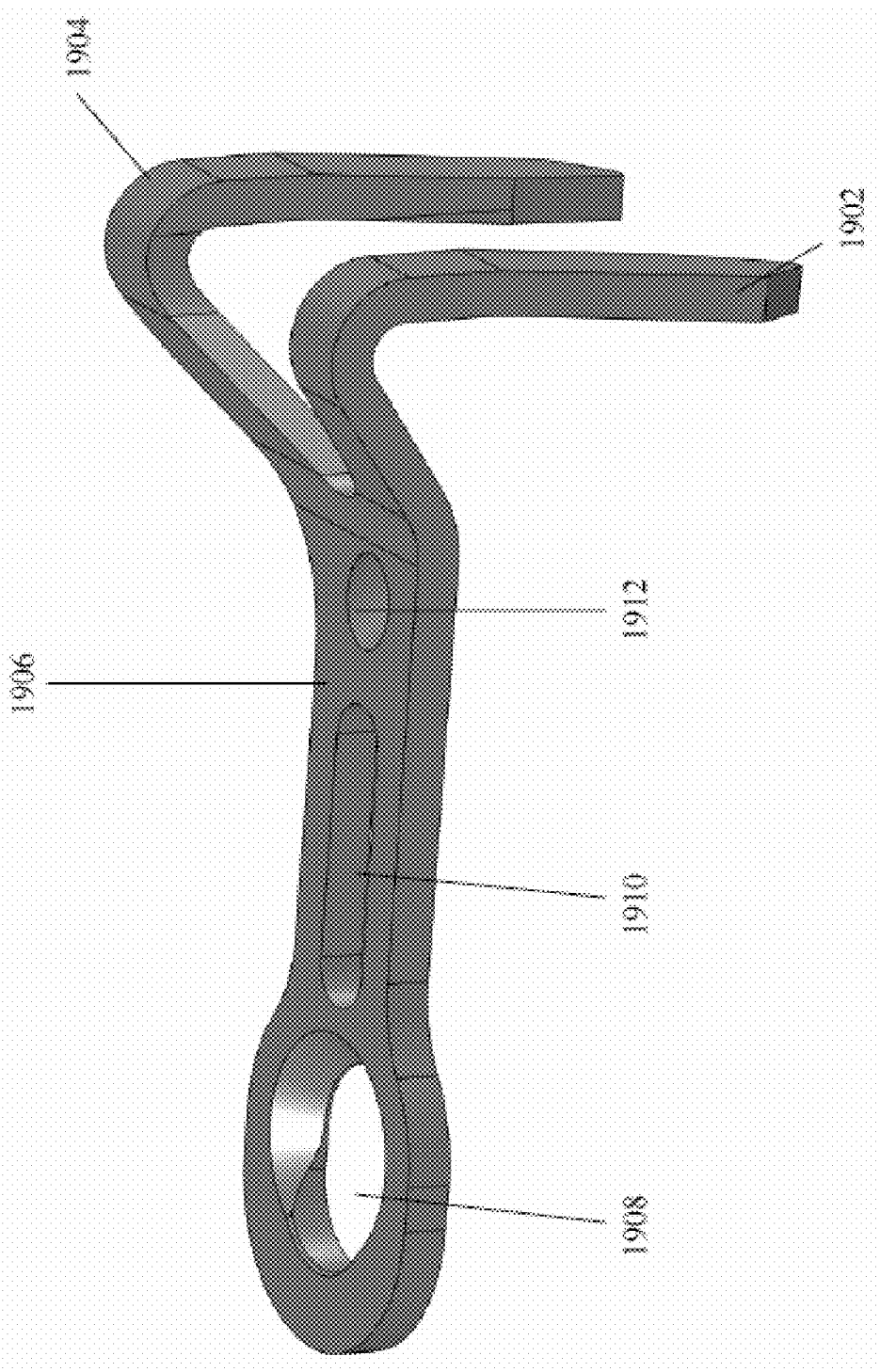
FIG. 19 illustrates an exemplary plate that is formed with a large step, in accordance with an embodiment.

FIG. 19 illustrates an exemplary plate that is formed with a large step, in accordance with an embodiment. Plate 1906 as shown operates functionally in a fashion similar to that of plate 206 described above and shown in FIG. 2. Members 1902 and 1904 as shown are bent and formed with a large step such that a portion of each of members 1902 and 1904 rises above the level of plate 1906 and bends perpendicularly with respect to plate 1906. The bend may be nearly perpendicular at an angle or approximately 80 to 85 degrees. Members 1902 and 1904 are configured to attach to a bone segment. Plate 1906 further includes a compression slot 1908 for receiving a compression screw that attaches to a bone segment. Plate 1906 further includes additional slots 1910 and 1912 for receiving additional screws should additional stability be required. Slot 1910 as shown is an elongated slot that may support at least one screw, and slot 1912 as shown is a circular slot supporting one screw for insertion into a bone segment.

Figure 20:
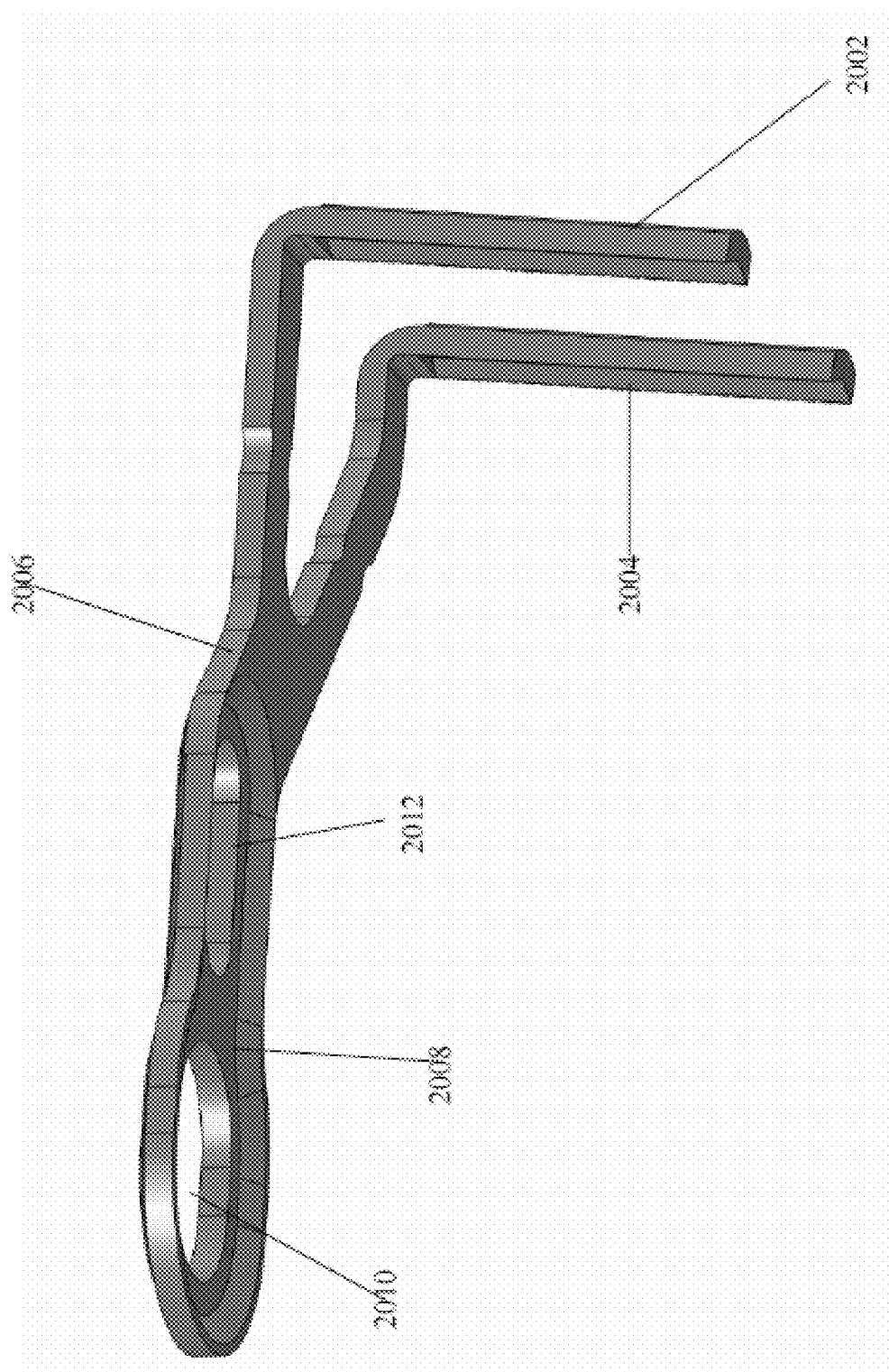
FIG. 20 illustrates an exemplary plate formed from a thin sheet, in accordance with an embodiment.

FIG. 20 illustrates an exemplary plate formed from a thin sheet, in accordance with an embodiment. Plate 2006 as shown operates functionally in a fashion similar to that of plate 206 described above and shown in FIG. 2. Members 2002 and 2004 as shown are configured for attachment with a bone segment. As plate 2006 is formed from a thin sheet of varying thickness, a slot section 2008 of plate 2006 including compression slot 2010 and additional slot 2012 are of a different thickness and thinner than the remainder of plate 2008 including members 2002 and 2004. Compression slot 2010 receives a bone screw which attaches to a bone segment. Additional slot 2012 may receive additional screws should additional stability be required.

Figure 21:
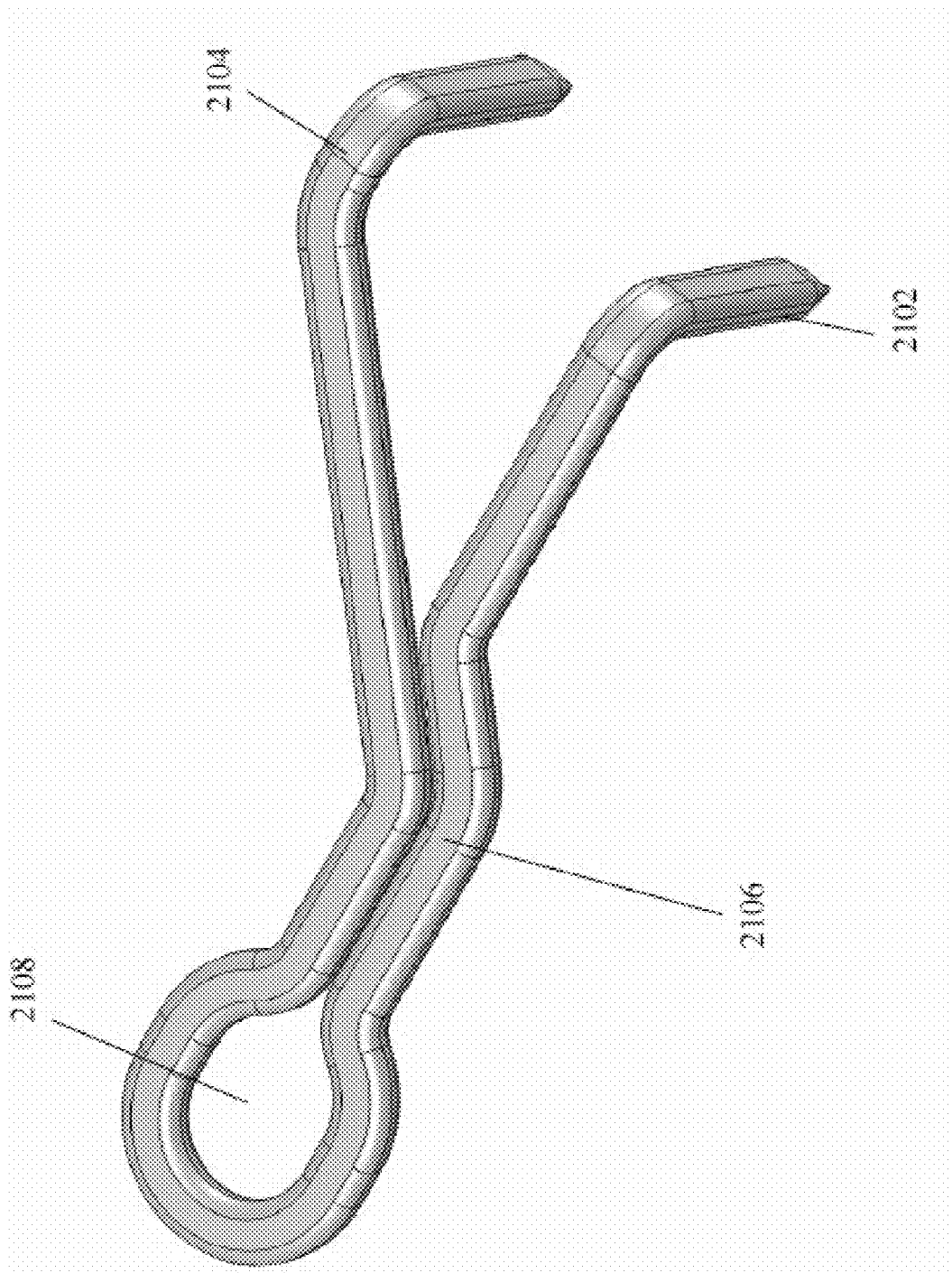
FIG. 21 illustrates an exemplary plate formed from a formed wire, in accordance with an embodiment.

FIG. 21 illustrates an exemplary plate formed from a formed wire, in accordance with an embodiment. Plate 2106 as shown operates functionally in a fashion similar to that of plate 206 described above and shown in FIG. 2. Plate 2106 as shown is formed from a single wire. Members 2102 and 2104 as shown are configured for attachment with a bone segment. Compression slot 2108 is shaped due to the bending of the wire of plate 2106 to form compression slot 2108 for receiving bone screws for attachment to a bone segment.

Figure 22:
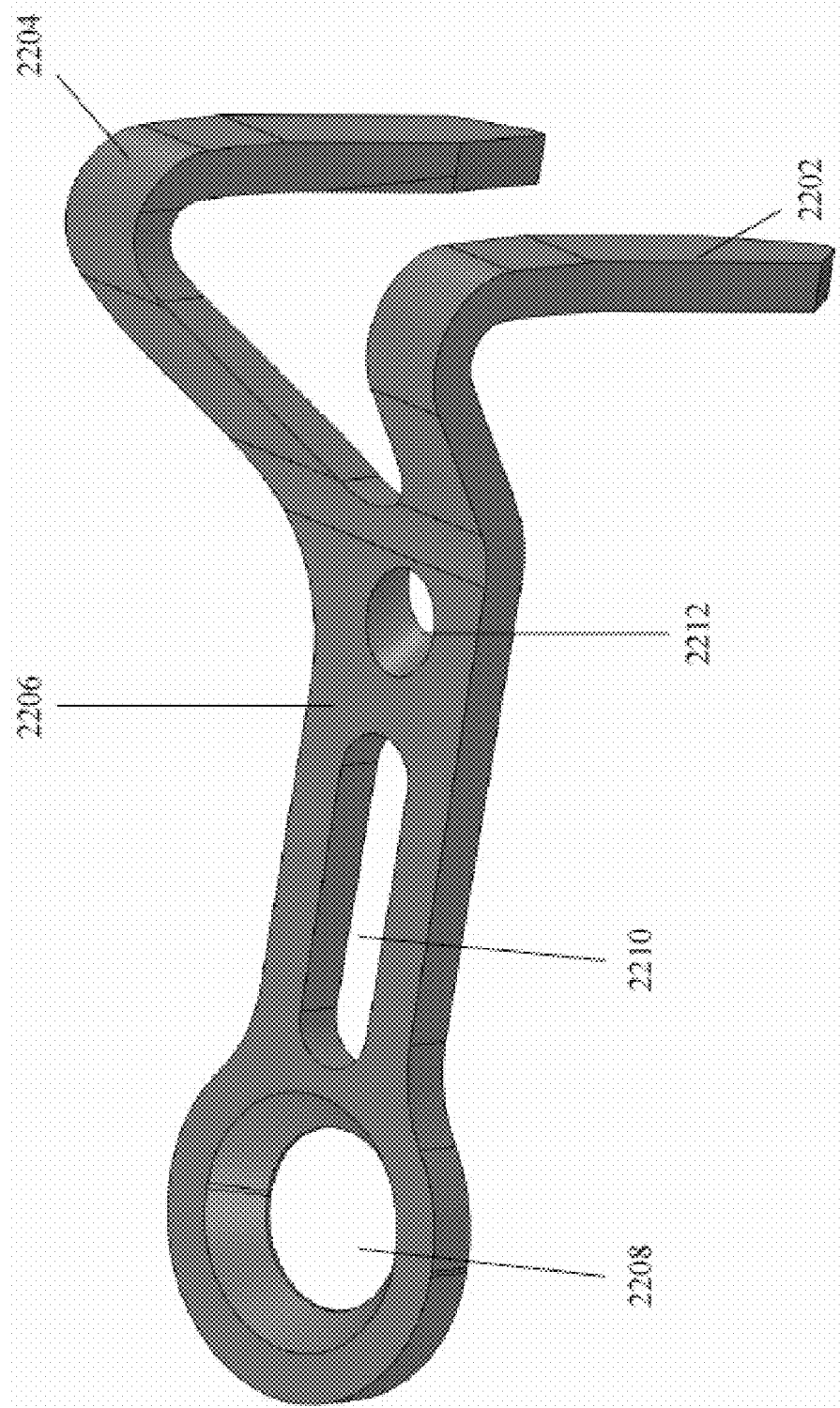
FIG. 22 illustrates an exemplary plate that is noncompressing and static, in accordance with an embodiment.

FIG. 22 illustrates an exemplary plate that is noncompressing and static, in accordance with an embodiment. Plate 2206 as shown operates functionally in a fashion similar to that of plate 1906 as described above and shown in FIG. 19. Members 2202 and 2204 as shown are bent and formed with a large step such that a portion of each of members 2202 and 2204 rises above the level of plate 2206 and bends perpendicularly with respect to plate 2206. Members 2202 and 2204 are configured to attach to a bone segment. Plate 2206 further includes a slot 2208 for receiving a bone screw that attaches to a bone segment. Plate 2206 is designed to be static and does not use compressive force to cause bone segments to move towards one another or fuse. Thus, slot 2208 is a noncompressive slot 2208 which receives a bone screw and does not affect compression with respect to the bone segments when the bone screw is screwed in. Plate 2206 further includes additional slots 2210 and 2212 for receiving additional screws should additional stability be required. Slot 2210 as shown is an elongated slot that may support at least one screw, and slot 2212 as shown is a circular slot supporting one screw for insertion into a bone segment.

Figure 23:
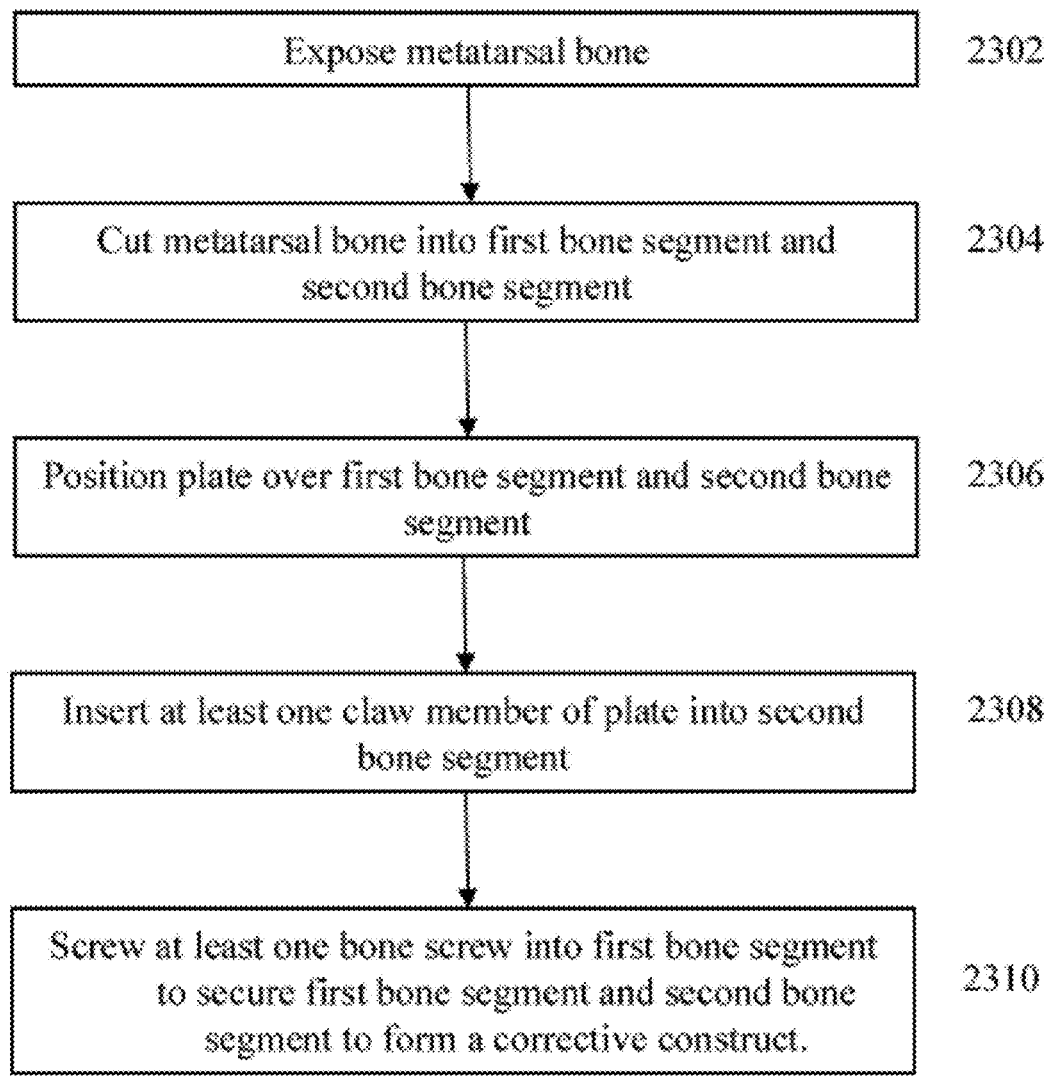
FIG. 23 illustrates an exemplary process for performing corrective surgery in accordance with an embodiment.

FIG. 23 illustrates an exemplary process for performing corrective bunionectomy surgery in accordance with an embodiment. At step 2302, corrective surgery on a bunion begins. At this point, a surgeon may operate on the foot of a patient, and expose the first metatarsal bone. While the process as depicted and as described relates to bunionectomy surgery, principles of the process and steps may also be applied to other bones or joints as needed and as understood by one of ordinary skill in the art.

At step 2304, the bone is cut into a first bone segment and a second bone segment based on the position of a guide used for cutting the bone. The position of the first bone segment and the second bone segment may then be offset to a desired correction distance, offset, or angle.

At step 2306, at least one hole is drilled into the second bone segment, and a plate is positioned over the first bone segment and the second bone segment such that at least one claw member of the plate is positioned to engage the second bone segment holes.

At step 2308, the at least one claw member of the plate is inserted into the second bone segment.

At step 2310, at least one bone screw is screwed into the first bone segment through at least one compression slot of the plate to secure the first bone segment and the second bone segment to form a corrective construct.

The embodiments described herein may also be used to stabilize broken or fragmented bones having fragments that are difficult to capture. An example may be periarticular fractures. For example, certain embodiments described herein may be used in an axial skeleton for fusion of vertebra by using compression. This will compress intervertebral spacers and keep them from being pushed out of place during loading. The embodiments described herein may also be used to fuse bone joints, typically after bone joint failure, when the bone joints have been stripped of articular cartilage.

Furthermore, any of the embodiments described herein are not meant to be limiting and any combination of features of the embodiments described herein that could or would be implemented by one of ordinary skill in the art should be recognized.

The foregoing Detailed Description is understood as being in every respect illustrative and exemplary, but not restrictive, and the scope of the embodiments disclosed herein is not to be determined from the Detailed Description, but rather from the claims as interpreted according to the full breadth permitted by the patent laws. It is understood that the embodiments shown and described herein are only illustrative of the principles of the present invention and that various modifications may be implemented by those skilled in the art without departing from the scope and spirit of the disclosure. Those skilled in the art could implement various other feature combinations without departing from the scope and spirit of the disclosure.

We claim:

1. A bone fixation system, comprising:
 a plate comprising:
  a first segment comprising:
   at least two members each including a first portion and a second portion angled with respect to the first portion and defining a free end, the second portions being and configured for engagement with a second bone segment; and
  a planar second segment that is elongated along a first direction comprising:
   at least one compression opening including a first radius at a first end, a second radius at a second end that is larger than the first radius, side surfaces tangentially connecting the first and second radii, and a chamfer such that the compression opening is configured for receiving at least one male fixation member therethrough and into a first bone segment so that the fixation member acts against the chamfer to translate the plate and thereby apply a compressive force to secure the first bone segment with the second bone segment to form a corrective construct; and
   at least one substantially circular fixation aperture,
   wherein the first portions of the at least two members comprise linear portions that diverge from each other as they extend from the second segment to the second portions along the first direction, and are coplanar with the second segment, and wherein the first portions of the at least two members form a void that extends therebetween that is elongated along the first direction.

2. The system of claim 1, wherein the first and second bone segments are segments of bone.

3. The system of claim 2, further comprising a guide configured to be placed over the bone and to facilitate cutting thereof into the first bone segment and the second bone segment.

4. The system of claim 3, wherein the plate is configured to be placed over the first bone segment and the second bone segment based on a corrective angle of the first bone segment and the second bone segment.

5. The system of claim 1, further comprising:
 a compressive force device configured to apply a compressive force to the at least two members causing engagement of the second portions of the at least two members with the second bone segment.

6. The system of claim 1, wherein the male fixation member is at least one of a screw, pin, bolt, or nail.

7. The system of claim 1, wherein a head portion of the male fixation member interacts with the chamfer of the compression opening proximate to the first radius after insertion therethrough to translate the plate.

8. The system of claim 1, further comprising:
 a stapling mechanism configured to apply a compressive force to the at least two members causing engagement of the second portions of the at least two members with the second bone segment.

9. The system of claim 8, wherein an angulation of the at least two members causes the at least two members to move downward as the plate is tightened such that the at least two members do not expulse from the bone.

10. The system of claim 1, wherein the second portions of the at least two members comprise fixation means for affixing to the second bone segment.

11. The system of claim 10, wherein the fixation means comprises at least one of: teeth, barbs, or a surface irregularity for securing to the second bone segment.

12. The system of claim 1, wherein the plate is an asymmetric plate.

13. The system of claim 1, wherein the at least two members are configured to be centralized after engagement with the second bone segment, and the at least two members are aligned with respect to each other in a coronal plane at a corrective shift based on the plate.

14. The system of claim 1, wherein the first segment and the second segment are connected by a hinged connection.

15. The system of claim 1, wherein the first segment and the second segment have a same thickness.

16. The system of claim 1, wherein the first segment and the second segment comprise a first material.

17. The system of claim 1, wherein the plate further comprises:
a third segment coupling the first segment and the second segment.

18. The system of claim 17, wherein the third segment comprises a first thickness and the first segment and the second segment comprise a second thickness.

19. The system of claim 17, wherein the third segment comprises a first material and the first segment and the second segment comprise a second material.

20. The system of claim 1, wherein the at least two members comprise a tine or a staple.

21. The system of claim 1, wherein the second portions of the at least two members are nearly perpendicular to an axis of the second bone segment.

22. The system of claim 1, wherein the first plate segment and the second plate segment form a Y-shape.

23. The system of claim 1, wherein the second portions of the at least two members extend perpendicularly from the respective first portions.

24. The system of claim 1, further including the at least one male fixation member, and wherein the at least one male fixation comprises at least one bone screw with an enlarged head portion.

25. The system of claim 24, wherein the second radius at the second end of the at least one compression opening matches the head portion of the at least one bone screw such that the second end supports a final position of the at least one bone screw.

26. The system of claim 25, wherein the compression opening is configured such that the at least one bone screw is screwed into the first bone segment through the at least one compression opening proximate to the first radius to affect compression between the first bone segment and the second bone segment by causing the plate to translate with respect to the at least one bone screw along a second direction that opposes the first direction to thereby pull the second bone segment towards the first bone segment.

27. The system of claim 25, wherein the first radius and second radius of the at least one compression slot are spaced along the first direction with the second radius being proximate to the first segment.

28. The system of claim 1, wherein the at least one compression opening is configured such that the fixation member acts against the chamfer to translate the plate along a second direction that opposes the first direction.

29. The system of claim 1, wherein the plate includes a concave end extending between the second portions of the first segment.

30. The system of claim 1, wherein the second portions of the first segment define an outermost end of the plate along the first direction.

31. A bone fixation system, comprising:
a plate comprising:
a first segment comprising:
at least two members each including a first portion and a second portion angled with respect to the first portion and defining a free end, the second portions being configured for engagement with a second bone segment; and
a boss hole extending through the first segment; and
a planar second segment that is elongated along a first direction comprising:
at least one compression slot positioned proximate to a first end of the second segment including a first radius at a first end, a second radius at a second end that is larger than the first radius, side surfaces connecting the first and second radii, and a chamfer such that the compression slot is configured to receive at least one bone screw therethrough proximate to the first radius and into a first bone segment such that a head portion of the at least one bone screw acts against the chamfer to translate the plate with respect to the at least one bone screw and thereby secure the first bone segment with the second bone segment to form a corrective construct; and
a boss positioned proximate to a second end of the second segment that is opposite the first end thereof and configured to engage the boss hole in the first segment and allow the first segment to rotate relative to the second segment,
wherein the first portions of the at least two members of the first segment are linear and diverge from each other as they extend from the second segment to the second portions along the first direction, and wherein the first portions of the at least two members form a void that extends therebetween that is elongated along the first direction.

32. The system of claim 31, wherein the second portions of the first segment define an outermost end of the plate along the first direction.

33. The system of claim 31, wherein the first portions of the first segment are coplanar with the second segment.

* * * * *

UNITED STATES PATENT AND TRADEMARK OFFICE
CERTIFICATE OF CORRECTION

PATENT NO. : 9,433,452 B2
APPLICATION NO. : 13/566517
DATED : September 6, 2016
INVENTOR(S) : Weiner et al.

Page 1 of 1

It is certified that error appears in the above-identified patent and that said Letters Patent is hereby corrected as shown below:

On the title page item (73), in the Assignee, Delete "NEXTREMITY SOLUTIONS, LLC" and insert
-- NEXTREMITY SOLUTIONS, INC. --

Signed and Sealed this
Fifteenth Day of November, 2016

Michelle K. Lee
*Director of the United States Patent and Trademark Office*